US006465513B1

(12) United States Patent
Grant et al.

(10) Patent No.: US 6,465,513 B1
(45) Date of Patent: Oct. 15, 2002

(54) MULTICYCLIC COMPOUNDS WHICH INHIBIT LEUKOCYTE ADHESION MEDIATED BY VLA-4

(75) Inventors: Francine S. Grant, Milpitas, CA (US); Bradley S. Johnson, San Francisco, CA (US); Michael A. Pleiss, Sunnyvale, CA (US); Eugene D. Thorsett, Half Moon Bay, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/489,157

(22) Filed: Jan. 21, 2000

Related U.S. Application Data
(60) Provisional application No. 60/117,743, filed on Jan. 29, 1999, and provisional application No. 60/116,735, filed on Jan. 22, 1999.

(51) Int. Cl.$^7$ .................. A01N 37/00; C07C 229/00
(52) U.S. Cl. .................. 514/529; 514/18; 514/19; 514/260; 562/507
(58) Field of Search .................. 514/18, 19, 529; 562/507

(56) References Cited

U.S. PATENT DOCUMENTS

| | | |
|---|---|---|
| 4,085,057 A | 4/1978 | Masuda et al. |
| 4,438,122 A | 3/1984 | Holmwood et al. |
| 4,505,910 A | 3/1985 | Bagli |
| 4,518,600 A | 5/1985 | Holmwood et al. |
| 4,544,402 A | 10/1985 | Schnurbusch et al. |
| 4,559,345 A | 12/1985 | Gomarasca et al. |
| 4,672,065 A | 6/1987 | Spatz |
| 4,908,368 A | 3/1990 | Murase et al. |
| 4,959,364 A | 9/1990 | Mueller et al. |
| 4,992,439 A | 2/1991 | Meanwell |
| 5,030,644 A | 7/1991 | Baldwin et al. |
| 5,120,734 A | 6/1992 | Klausener et al. |
| 5,238,934 A | 8/1993 | Knüppel et al. |
| 5,278,184 A | 1/1994 | Artico et al. |
| 5,510,332 A | 4/1996 | Kogan et al. |
| 5,580,868 A | 12/1996 | Lunkenheimer et al. |
| 5,770,573 A | * 6/1998 | Arrhenius et al. |
| 5,814,643 A | 9/1998 | Duggan et al. |
| 5,821,231 A | * 10/1998 | Arrhenius et al. |
| 5,861,429 A | 1/1999 | Sato et al. |
| 5,925,644 A | 7/1999 | Jakobi et al. |
| 5,942,504 A | 8/1999 | Grobelny |
| 5,955,491 A | 9/1999 | Sohda et al. |
| 5,962,479 A | 10/1999 | Chen |
| 5,972,946 A | 10/1999 | Murata et al. |
| 6,005,117 A | 12/1999 | Wehner et al. |

FOREIGN PATENT DOCUMENTS

| | | |
|---|---|---|
| DE | 197 13 000 | 10/1998 |
| EP | 0 330 506 | 8/1989 |
| WO | 96/01644 | 1/1996 |
| WO | 99/64390 | 2/1999 |
| WO | 99/10312 | 3/1999 |
| WO | 99/10313 | 3/1999 |
| WO | 99/52898 | 10/1999 |
| WO | 00/43354 | 7/2000 |

OTHER PUBLICATIONS

Abraham, et al., $\alpha_4$–Integrins Mediate Antigen–Induced Late Brochial Responses and Prolonged Airway Hyperresponsiveness in Sheep, J. Clin. Invest., 93:776–787 (1994).
Bao, et al., Correlation of VLA–4 Integrin Expression with Metastatic Potential in Various Human Tumor Cell Lines, Diff., 52–239–246 (1993).
Baron, et al., Surface Expression of $\alpha$4 Integrin by CD4 T Cells is Required for Their Entry into Brain Parenchyma, J. Exp. Med., 177:57–68 (1993).
Baron, et al., The Pathogenesis of Adoptive Murine Autoimmune Diabetes Requires an Interaction between $\alpha$4–Integrins and Vascular Cell Adhesion Molecule–1, J. Clin. Invest., 93:1700–1708 (1994).
Burkly, et al., Protection Against Adoptive Transfer of Antoimmune Diabetes Mediated Through Very Late Antigen–4 Integrin, Diabetes, 43:529–534 (1994).
Cybulsky, et al., Endothelial Expression of a Mononuclear Leukocyte Adhesion Molecule during Atherogenesis, Science, 251:788–791 (1991).
Elices, et al., Expression and Functional Signficance of Alternatively Spliced CS1 Fibronectin in Rheumatoid Arthritis Microvasculature, J. Clin. Invest., 93:405–416 (1994).
Elices, et al., VCAM–1 on Activated Endothelium Interacts with the Leukocyte Integrin VLA–4 at a Site Distinct from the VLA–4/Fibronectin Binding Site, Cell, 60:577–584 (1990).
Hamann, et al., Role of $\alpha_4$–Integrins in Lymphocyte Homing to Mucosal Tissues In Vivo, J. Immunology, 152:3283–3292 (1994).
Kawaguchi, et al., VLA–4 Molecules on Tumor Cells Initate an Adhesive Interaction with VCAM–1 Molecules on Endothelial Cell Surface, Japanese J. Cancer Res., 83:1304–1316 (1992).

(List continued on next page.)

Primary Examiner—Alan L. Rotman
Assistant Examiner—Héctor M Reyes
(74) Attorney, Agent, or Firm—Burns, Doane, Swecker & Mathis LLP

(57) ABSTRACT

Disclosed are compounds which bind VLA-4. Certain of these compounds also inhibit leukocyte adhesion and, in particular, leukocyte adhesion mediated by VLA-4. Such compounds are useful in the treatment of inflammatory diseases in a mammalian patient, e.g., human, such as asthma, Alzheimer's disease, atherosclerosis, AIDS dementia, diabetes, inflammatory bowel disease, rheumatoid arthritis, tissue transplantation, tumor metastasis and myocardial ischemia. The compounds can also be administered for the treatment of inflammatory brain diseases such as multiple sclerosis.

14 Claims, No Drawings

OTHER PUBLICATIONS

Lauri, et al., Decreased Adhesion to Endothelial Cells and Matrix of H–2K$^b$ Gene Transfected Tumor Cells, British J. Cancer, 68:862–687 (1993).

Li, et al., An Atherogenic Diet Rapidly Induces VCAM–1, a Cytokine–Regulatable Mononuclear Leukocyte Adhesion Molecule, in Rabbit Aortic Endothelium, Arterioscler. Thromb., 13:197–204 (1993).

Okarhara, et al., Involvement of Very Late Activation Antigen 4 (VLA–4) and Vascular Cell Adhesion Molecule 1 (VCAM–1) in Tumor Necrosis Factor α Enhancement of Experimental Metastasis, Can. Res., 54:3233–3236 (1994).

Osborn, Leukocyte Adhesion to Endothelium in Inflammation, Cell, 62:3–6 (1990).

Paavonen, et al., In Vivo Evidence of the Role of $\alpha_4\alpha_1$VCAM–1 Interaction in Sarcoma, but nit in Carcinoma Extravasation, Int. J. Can., 58:298–302 (1994).

Paul, et al., Monoclonal Antibodies Against LFA–1 and VLA–4 Inhibit Graft Vasculitis in Rat Cardiac Allogrfts, Transpl. Proceed., 25:813–814 (1993).

Postigo, et al., Increased Binding of Synovial T Lymphocytes from Rheumatoid Arthritis to Endothelial–Leukocyte Adhesion Molecule–1 (ELAM–1) and Vascular Cell Adhesion Molecule–1 (VCAM–1), J. Clin. Invest., 89:1445–1452 (1992).

Pretolani, et al., Antibody to Very Late Activation Antigen 4 Prevents Antigen–induced Bronchial Hyperreactivity and Cellular Infiltration in the Guinea Pig Airways, J. Exp. Med., 180:795–805 (1994).

Sasseville, et al., Monocyte Adhesion to Endothelium in Simian Immunodeficiency Virus–Induced AIDS Encephalitis is Mediated by Vascular Cell Adhesion Molecule–1/α4β1 Integrin Interactions, Am. J. Path., 144:27 (1994).

Schadendorf, et al., Tumor Progression and Metastatic Behavior In Vivo Correlates with Integrin Expression in Melanocytic Tumors, J. Path., 170:429–434 (1993).

Springer, Adhesion Receptors of the Immune System, Nature, 346:425–434 (1990).

van Dinther–Janssen, et al., Role of the CS1 Adhesion Motif of Fibronectin in T Cell Adhesion to Synovial Membrane and peripheral Lymph Node Endothelium, Annals. Rheumatic Dis., 52:672–676 (1993).

van Dinther–Janssen, et al., The VLA–4/VCAM–1 Pathway is Involved in Lyphocyte Adhesion to Endothelium in Rheumatoid Synovium, J. Immunology, 147:4207–4210 (1991).

Yang, et al., Inhibition of Insulitis and Prevention of Diabetes in Nonobese Diabetic Mice by Blocking L–Selectin and Very Late Antigen 4 Adhesion Receptors, Proc. Nat. Acad. Science (USA), 90:10494–10498 (1993).

Yednock, et al., Prevention of Experimental Autoimmune Encephalomyelitis by Antibodies Against α4β1 Integrin, Nature, 356:63–66 (1992).

* cited by examiner

MULTICYCLIC COMPOUNDS WHICH INHIBIT LEUKOCYTE ADHESION MEDIATED BY VLA-4

CROSS-REFERENCE TO RELATED APPLICATIONS

This application claims the benefit of U.S. Patent Application No. 60/116,735, filed Jan. 22, 1999, and U.S. Patent Application No. 60/117,743, filed Jan. 29, 1999; the disclosures of which are incorporated herein by reference in their entirety.

BACKGROUND OF THE INVENTION

Field of the Invention

This invention relates to compounds which inhibit leukocyte adhesion and, in particular, leukocyte adhesion mediated by VLA-4.

References

The following publications, patents and patent applications are cited in this application as superscript numbers:

[1] Hemler and Takada, *European Patent Application Publication* No. 330,506, published Aug. 30, 1989
[2] Elices, et al., *Cell*, 60:577–584 (1990)
[3] Springer, *Nature*, 346:425–434 (1990)
[4] Osborn, *Cell*, 62:3–6 (1990)
[5] Vedder, et al., *Surgery*, 106:509 (1989)
[6] Pretolani, et al., *J. Exp. Med.*, 180:795 (1994)
[7] Abraham, et al., *J. Clin. Invest.*, 93:776 (1994)
[8] Mulligan, et al., *J. Immunology*, 150:2407 (1993)
[9] Cybulsky, et al., *Science*, 251:788 (1991)
[10] Li, et al., *Arterioscler. Thromb.*, 13:197 (1993)
[11] Sasseville, et al., *Am. J. Path.*, 144:27 (1994)
[12] Yang, et al., *Proc. Nat. Acad. Science (USA)*, 90:10494 (1993)
[13] Burkly, et al., *Diabetes*, 43:529 (1994)
[14] Baron, et al., *J. Clin. Invest.*, 93:1700 (1994)
[15] Hamann, et al., *J. Immunology*, 152:3238 (1994)
[16] Yednock, et al., *Nature*, 356:63 (1992)
[17] Baron, et al., *J. Exp. Med.*, 177:57 (1993)
[18] van Dinther-Janssen, et al., *J. Immunology*, 147:4207 (1991)
[19] van Dinther-Janssen, et al., *Annals. Rheumatic Dis.*, 52:672 (1993)
[20] Elices, et al., *J. Clin. Invest.*, 93:405 (1994)
[21] Postigo, et al., *J. Clin. Invest.*, 89:1445 (1991)
[22] Paul, et al., *Transpl. Proceed.*, 25:813 (1993)
[23] Okarhara, et al., *Can. Res.*, 54:3233 (1994)
[24] Paavonen, et al., *Int. J. Can.*, 58:298 (1994)
[25] Schadendorf, et al., *J. Path.*, 170:429 (1993)
[26] Bao, et al., *Diff.*, 52:239 (1993)
[27] Lauri, et al., *British J. Cancer*, 68:862 (1993)
[28] Kawaguchi, et al., *Japanese J. Cancer Res.*, 83:1304 (1992)
[29] Kogan, et al., U.S. Pat. No. 5,510,332, issued Apr. 23, 1996
[30] International Patent Appl. Publication No. WO 96/01644

All of the above publications, patents and patent applications are herein incorporated by reference in their entirety to the same extent as if each individual publication, patent or patent application was specifically and individually indicated to be incorporated by reference in its entirety.

State of the Art

VLA-4 (also referred to as $\alpha_4\beta_1$ integrin and CD49d/CD29), first identified by Hemler and Takada[1] is a member of the β1 integrin family of cell surface receptors, each of which comprises two subunits, an α chain and a β chain. VLA4 contains an α4 chain and a β1 chain. There are at least nine β1 integrins, all sharing the same β1 chain and each having a distinct α chain. These nine receptors all bind a different complement of the various cell matrix molecules, such as fibronectin, laminin, and collagen. VLA-4, for example, binds to fibronectin. VLA-4 also binds non-matrix molecules that are expressed by endothelial and other cells. These non-matrix molecules include VCAM-1, which is expressed on cytokine-activated human umbilical vein endothelial cells in culture. Distinct epitopes of VLA-4 are responsible for the fibronectin and VCAM-1 binding activities and each activity has been shown to be inhibited independently.[2]

Intercellular adhesion mediated by VLA-4 and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[3] and Osborn[4].

Inflammatory brain disorders, such as experimental autoimmune encephalomyelitis (EAE), multiple sclerosis (MS) and meningitis, are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis.

In other organ systems, tissue damage also occurs via an adhesion mechanism resulting in migration or activation of leukocytes. For example, it has been shown that the initial insult following myocardial ischemia to heart tissue can be further complicated by leukocyte entry to the injured tissue causing still further insult (Vedder et al.[5]). Other inflammatory conditions mediated by an adhesion mechanism include, by way of example, asthma[6-8], Alzheimer's disease, atherosclerosis[9-10], AIDS dementia[11], diabetes[12-14] (including acute juvenile onset diabetes), inflammatory bowel disease[15] (including ulcerative colitis and Crohn's disease), multiple sclerosis[16-17], rheumatoid arthritis[18-21], tissue transplantation[22], tumor metastasis[23-28], meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

In view of the above, assays for determining the VLA-4 level in a biological sample containing VLA-4 would be useful, for example, to diagnosis VLA-4 mediated conditions. Additionally, despite these advances in the understanding of leukocyte adhesion, the art has only recently addressed the use of inhibitors of adhesion in the treatment of inflammatory brain diseases and other inflammatory conditions[29,30]. The present invention addresses these and other needs.

SUMMARY OF THE INVENTION

This invention provides compounds which bind to VLA-4. Such compounds can be used, for example, to assay for the presence of VLA-4 in a sample and in pharmaceutical compositions to inhibit cellular adhesion mediated by VLA-4, for example, binding of VCAM-1 to VLA-4. The compounds of this invention have a binding affinity to VLA-4 as expressed by an $IC_{50}$ of about 15 μM or less (as measured using the procedures described in Example A below) which compounds are defined by formula I:

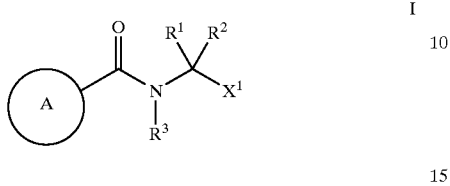

wherein
ring A is a multicyclic bridged cycloalkyl, multicyclic bridged cycloalkenyl or multicyclic bridged heterocyclic group provided the multicyclic bridged heterocyclic group does not contain a lactam and further wherein said multicyclic bridged cycloalkyl, multicyclic bridged cycloalkenyl or multicyclic bridged heterocyclic group is optionally substituted, on any ring atom capable of substitution, with 1–3 substituents selected from the group consisting of alkyl, substituted alkyl, alkoxy, substituted alkoxy, acyl, acylamino, thiocarbonyl-amino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where each R is independently hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, —N[S(O)$_2$—R']$_2$ and —N[S(O)$_2$—NR']$_2$ where each R' is independently selected from the group consisting of alkyl, substituted alkyl, aryl, substituted aryl, heteroaryl, substituted heteroaryl, heterocyclic and substituted heterocyclic, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl;

$R^1$ is selected from the group consisting of:
(a) —(CH$_2$)$_x$—Ar—$R^5$ where $R^5$ is selected from the group consisting of —O—Z—NR$^6$R$^{6'}$ and —O—Z—R$^7$ wherein $R^6$ and $R^{6'}$ are independently selected from the group consisting of hydrogen, alkyl, substituted alkyl, cycloalkyl, substituted cycloalkyl, heterocyclic, substituted heterocyclic, and where $R^6$ and $R^{6'}$ are joined to form a heterocycle or a substituted heterocycle, $R^7$ is selected from the group consisting of heterocycle and substituted heterocycle, and Z is selected from the group consisting of —C(O)— and —SO$_2$—, Ar is aryl, heteroaryl, substituted aryl or substituted heteroaryl, x is an integer of from 1 to 4;
(b) Ar$^1$—Ar$^2$—C$_{1-10}$alkyl-, Ar$^1$—Ar$^2$—C$_{2-10}$alkenyl- and Ar$^1$—Ar$^2$—C$_{2-10}$alkynyl-, wherein Ar$^1$ and Ar$^2$ are independently aryl or heteroaryl each of which is optionally substituted with one to four substituents independently selected from R$^b$; alkyl, alkenyl and alkynyl are optionally substituted with one to four substituents independently selected from R$^a$;
(c) —(CH$_2$)$_x$—Ar—$R^8$, wherein $R^8$ is heterocyclic or substituted heterocyclic;

Ar is aryl, heteroaryl, substituted aryl or substituted heteroaryl, x is an integer of from 1 to 4;
(d) —(CH$_2$)$_x$—Ar—$R^9$, wherein $R^9$ is —C$_{1-10}$alkyl, —C$_{2-10}$alkenyl or —C$_{2-10}$alkynyl, wherein alkyl, alkenyl and alkynyl are optionally substituted with one to four substituents selected from R$^a$;

Ar is aryl, heteroaryl, substituted aryl or substituted heteroaryl, x is an integer of from 1 to 4;
(e) —(CH$_2$)$_x$—Cy, wherein Cy is optionally substituted with 1 to 4 substitutents selected from $R^2$ is selected from the group consisting of hydrogen, C$_{1-10}$ alkyl, C$_{2-10}$ alkenyl, C$_{2-10}$ alkynyl, aryl, aryl C$_{1-10}$alkyl, heteroaryl, and heteroaryl C$_{1-10}$ alkyl, wherein alkyl, alkenyl and alkynyl are optionally substituted with one to four substituents selected from R$^a$, and aryl and heteroaryl are optionally substituted with one to four substituents independently selected from R$^b$;

$R^3$ is selected from the group consisting of hydrogen, C$_{1-10}$ alkyl optionally substituted with one to four substituents independently selected from $R^a$ and Cy optionally substituted with one to four substituents independently selected from $R^b$;

$R^a$ is selected from the group consisting of Cy, —$OR^d$, —$NO_2$, halogen —$S(O)_mR^d$, —$SR^d$, —$S(O)_2OR^d$, —$S(O)_mNR^dR^e$, —$NR^dR^e$, —$O(CR^fR^g)_nNR^dR^e$, —$C(O)R^d$, —$CO_2R^d$, —$CO_2(CR^fR^g)_nCONR^dR^e$, —$OC(O)R^d$, —CN, —$C(O)NR^dR^e$, —$Nr^dC(O)R^e$, —$OC(O)NR^dR^e$, —$NR^dC(O)OR^e$, —$NR^dC(O)NR^dR^e$, —$CR^d(N-OR^e)$, $CF_3$, and —$OCF_3$; wherein Cy is optionally substituted with one to four substituents independently selected from $R^c$;

$R^b$ is selected from the group consisting of $R^a$, $C_{1-10}$ alkyl, $C_{2-10}$ alkenyl, $C_{2-10}$ alkynyl, aryl $C_{1-10}$ alkyl, heteroaryl, $C_{1-10}$alkyl, wherein alkyl, alkenyl, aryl, heteroaryl are optionally substituted with a group independently selected from $R^c$;

$R^c$ is selected from the group consisting of halogen, amino, carboxy, $C_{1-4}$ alkyl, $C_{1-4}$ alkoxy, aryl, aryl $C_{1-4}$-alkyl, hydroxy, $CF_3$, and aryloxy;

$R^d$ and $R^e$ are independently selected from hydrogen, $C_{1-10}$ alkyl, $C_{2-10}$ alkenyl, $C_{2-10}$ alkynyl, Cy and Cy—$C_{1-10}$alkyl, wherein alkyl, alkenyl, alkynyl and Cy are optionally substituted with one to four substituents independently selected from $R^c$; or $R^d$ and $R^e$ together with the atoms to which they are attached form a heterocyclic ring of 5 to 7 members containing 0–2 additional heteroatoms independently selected from oxygen, sulfur and nitrogen;

$R^f$ and $R^g$ are independently selected from hydrogen, $C_{1-10}$ alkyl, Cy and Cy—$C_{1-10}$ alkyl; or $R^f$ and $R^g$ together with the carbon to which they are attached form a ring of 5 to 7 members containing 0–2 heteroatoms independently selected from oxygen, sulfur and nitrogen;

$R^h$ is selected from the group consisting of hydrogen, $C_{1-10}$ alkyl, $C_{2-10}$ alkenyl, $C_{2-10}$ alkynyl, cyano, aryl, aryl $C_{1-10}$ alkyl, heteroaryl, heteroaryl $C_{1-10}$ alkyl, or —$SO_2R^i$; wherein alkyl, alkenyl, and alkynyl are optionally substituted with one to four substitutents independently selected from $R^a$; and aryl and heteroaryl are each optionally substituted with one to four substituents independently selected from $R^b$;

$R^i$ is selected from the group consisting of $C_{1-10}$ alkyl, $C_{2-10}$ alkenyl, $C_{2-10}$ alkynyl, and aryl; wherein alkyl, alkenyl, alkynyl and aryl are each optionally substituted with one to four substituents independently selected from $R^c$;

Cy is cycloalkyl, heterocyclyl, aryl, or heteroaryl;

$X^1$ is selected from the group consisting of —$C(O)OR^d$, —$P(O)(OR^d)(OR^e)$, —$P(O)(R^d)(OR^e)$, —$S(O)_mOR^d$, —$C(O)NR^dR^h$, and -5-tetrazolyl;

m is an integer from 1 to 2;

n is an integer from 1 to 10;

and pharmaceutically acceptable salts thereof.

Preferred compounds of this invention are represented by formula II:

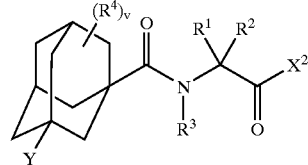

wherein $R^1$, $R^2$ and $R^3$ are as defined herein;

Y is selected from the group consisting of hydrogen, $R^d$, Cy, —$OR^d$, —$NO_2$, halogen, —$S(O)_mR^d$, —$SR^d$, —$S(O)_2OR^d$, —$S(O)_mNR^dR^e$, —$NR^dR^e$, —$O(CR^fR^g)_nNR^dR^e$, —$C(O)R^d$, —$CH(OH)R^d$, —$CO_2R^d$, —$CO_2(CR^fR^g)_nCONR^dR^e$, —$OC(O)R^d$, —CN, —$C(O)NR^dR^e$, —$NR^dC(O)R^e$, —$OC(O)NR^dR^e$, —$NR^dC(O)OR^e$, —$NR^dC(O)NR^dR^e$, —$CR^d(N-OR^e)$, $CF_3$, and —$OCF_3$; wherein Cy is optionally substituted with one to four substituents independently selected from $R^c$; where Cy, $R^c$, $R^d$, $R^e$, $R^f$, $R^g$, $R^h$, m and n are as defined herein;

$R^4$ is selected from the group consisting of alkyl, substituted alkyl, alkoxy, substituted alkoxy, acyl, acylamino, thiocarbonyl-amino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where each R is independently hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, —$N[S(O)_2$—R']$_2$ and —$N[S(O)_2$—NR']$_2$ where each R' is independently selected from the group consisting of alkyl, substituted alkyl, aryl, substituted aryl, heteroaryl, substituted heteroaryl, heterocyclic and substituted heterocyclic, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsynmmetric di-substituted amines having different substituents selected from alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl; or R$^b$ where R$^b$ is as defined herein;

X$^2$ is selected from the group consisting of hydroxyl, alkoxy, substituted alkoxy, alkenoxy, substituted alkenoxy, cycloalkoxy, substituted cycloalkoxy, cycloalkenoxy, substituted cycloalkenoxy, aryloxy, substituted aryloxy, heteroaryloxy, substituted heteroaryloxy, heterocyclyloxy, substituted heterocyclyloxy and —NR"R" where each R" is independently selected from the group consisting of hydrogen, alkyl, substituted alkyl, alkenyl, substituted alkenyl, cycloalkyl, substituted cycloalkyl, aryl, substituted aryl, heteroaryl, substituted heteroaryl, heterocyclic and substituted heterocyclic; or R$^d$ where R$^d$ is as defined herein;

v is an integer ranging from 0 to 3; and pharmaceutically acceptable salts thereof.

In formula I and II above, when X$^1$ is —CO$_2$R$^d$ and R$^d$ is other than hydrogen or X$^2$ is other than —OH, or pharmaceutical salts thereof, R$^d$ and X$^2$ are preferably a substituent which will convert (e.g., hydrolyze, metabolize, etc.) in vivo to a compound where R$^d$ is hydrogen or X$^2$ is —OH, or salts thereof. Accordingly, suitable X$^2$ groups are any art recognized pharmaceutically acceptable groups which will hydrolyze or otherwise convert in vivo to a hydroxyl group or a salt thereof including, by way of example, esters (X$^2$ is alkoxy, substituted alkoxy, cycloalkoxy, substituted cycloalkoxy, alkenoxy, substituted alkenoxy, cycloalkenoxy, substituted cycloalkenoxy, aryloxy, substituted aryloxy, heteroaryloxy, substituted heteroaryloxy, heterocyclooxy, substituted heterocyclooxy, and the like).

In the compounds of formula I, ring A is preferably a multicyclic bridged cycloalkyl, multicyclic bridged cycloalkenyl or multicyclic bridged heterocyclic group having a steric volume which is approximately equal to that of adamantane or adamantanecarboxylic acid methyl ester (without considering any additional substituents present on the ring), i.e., ± about 20%, preferably ±10% of the steric volume of adamantane or adamantanecarboxylic acid methyl ester. Numerous ways exist for estimating steric volume. Comparison of Corey-Pauling-Kolton (CPK) space filling models can be utilized to determine steric volume (described, for example, in A. Leo et al., *J. Med. Chem.* 1976, 19, 611–615). A more accurate value can be calculated from the crystal structure (described, for example, in R S Bohacek and W C Guida, *J. Mol. Graph.* 1989, 7, 113–117) and compared to that known for adamantane (described, for example, in J. P. Amoureux and M. Foulon, *Acta Cryst.* 1987, B43, 470–479) or adamantanecarboxylic acid (described, for example, in P. Harvey et al., *Can. J. Chem.* 1990, 68, 1163–1169). Molecular modeling programs can also be utilized to calculate and compare steric volumes (described, for example, in B. B. Masek et al., *J. Med. Chem.* 1993, 36, 1230–1238 and those cited in reference 1 of this publication). Additionally, numerous physicochemical and theoretical parameters have been described and shown to be accurate predictors of overall steric volume. Molar refractivity (MR) is one such parameter. MR has been studied extensively and is regarded as a good predictor of steric volume since it is directly proportional to molecular weight. Molar refractivity is described, for example, in C. Hansch et al., *Exploring QSAR, Fundimentals and Applications in Chemistry and Biology*, S. Heller, Editor, American Chemical Society, p. 78–85, 1995, and can be calculated using PC Models Program, Version 4.6.1, available from Daylight Chemical Information Systems, 419 Palace Ave., Santa Fe, N. Mex. 87501 USA, or using the tables found in C. Hansch et al. on pages 81–84. In this regard, ring A has a molar refractivity (MR) ranging from about 2.86 to about 6.68, preferably from about 3.34 to about 6.2.

Preferred ring A groups include, by way of illustration, adamantyl, quinuclidine and the like.

In a preferred embodiment of this invention, R$^1$ is selected from all possible isomers arising by substitution with the following groups:

3-[(CH$_3$)$_2$NC(O)O-]benzyl,
4-[(CH$_3$)$_2$NC(O)O-]benzyl,
4-[(CH$_3$)$_2$NS(O)$_2$O-]benzyl,
4-[(piperidin-1'-yl)C(O)O-]benzyl,
4-[(piperidin-4'-yl)C(O)O-]benzyl,
4-[(1'-methylpiperidin-4'-yl)C(O)O-]benzyl,
4-[(4'-hydroxypiperidin-1'-yl)C(O)O-]benzyl,
4-[(4'-formyloxypiperidin-1'-yl)C(O)O-]benzyl,
4-[(4'-ethoxycarbonylpiperidin-1'-yl)C(O)O-]benzyl,
4-[(4'-carboxylpiperidin-1'-yl)C(O)O-]benzyl,
4-[(3'-hydroxymethylpiperidin-1'-yl)C(O)O-]benzyl,
4-[(4'-hydroxymethylpiperidin-1'-yl)C(O)O-]benzyl,
4-[(4'-phenyl-1'-Boc-piperidin-4'-yl)-C(O)O-]benzyl,
4-[(4'-piperidon-1-'-yl ethylene ketal)C(O)O-]benzyl,
4-[(piperazin-4'-yl)-C(O)O-]benzyl,
4-[(1'-Boc-piperazin-4'-yl)-C(O)O-]benzyl,
4-[(4'-methylpiperazin-1'-yl)C(O)O-]benzyl,
4-[(4'-methylhomopiperazin-1'-yl)C(O)O-]benzyl,
4-[(4'-(2-hydroxyethyl)piperazin-1'-yl)C(O)O-]benzyl,
4-[(4'-phenylpiperazin-1'-yl)C(O)O-]benzyl,
4-[(4'-(pyridin-2-yl)piperazin-1'-yl)C(O)O-]benzyl,
4-[(4'-(4-trifluoromethylpyridin-2-yl)piperazin-1'-yl)C(O)O-]benzyl,
4-[(4'-(pyrimidin-2-yl)piperazin-1'-yl)C(O)O-]benzyl,
4-[(4'-acetylpiperazin-1'-yl)C(O)O-]benzyl,
4-[(4'-(phenylC(O)-)piperazin-1'-yl)C(O)O-]benzyl,
4-[(4'-(pyridin-4-ylC(O)-)piperazin-1'-yl)C(O)O-]benzyl,
4-[(4'-(phenylNHC(O)-)piperazin-1'-yl)C(O)O-]benzyl,
4-[(4'-(phenylNHC(S)-)piperazin-1'-yl)C(O)O-]benzyl,
4-[(4'-methanesulfonylpiperazin-1'-yl-C(O)O-)benzyl,
4-[(4'-trifluoromethanesulfonylpiperazin-1'-yl-C(O)O-)benzyl,
4-[(morpholin-4'-yl)C(O)O-]benzyl,
3-nitro-4-[(morpholin-4'-yl)-C(O)O-]benzyl,
4-[(thiomorphlin-4'-yl)C(O)O-]benzyl,
4-[(thiomorpholin-4'-yl sulfone)-C(O)O-]benzyl, (alternative nomenclature 4-[(1,1-dioxothiomorpholin-4-yl)-C(O)O-]benzyl),
4-[(pyrrolidin-1'-yl)C(O)O-]benzyl,
4-[(2'-methylpyrrolidin-1'-yl)C(O)O-]benzyl,
4-[(2'-(methoxycarbonyl)pyrrolidin-1'-yl)C(O)O-]benzyl, 4-[(2'-(hydroxymethyl)pyrrolidin-1'-yl)C(O)O-]benzyl,
4-[(2'-(N,N-dimethylamino)ethyl)(CH₃)NC(O)O-]benzyl,
4-[(2'-(N-methyl-N-toluene-4-sulfonylamino)ethyl)(CH₃)N—C(O)O-]benzyl,
4-[(2'-(morpholin-4'-yl)ethyl)(CH₃)NC(O)O-]benzyl,
4-[(2'-(hydroxy)ethyl)(CH₃)NC(O)O-]benzyl,
4-[bis(2'-(hydroxy)ethyl)NC(O)O-]benzyl,
4-[(2'-(formyloxy)ethyl)(CH₃)NC(O)O-]benzyl,
4-[(CH₃OC(O)CH₂)HNC(O)O-]benzyl,
4-[2'-(phenylNHC(O)O-)ethyl-]HNC(O)O-]benzyl,
3-chloro-4-[(CH₃)₂NC(O)O-]benzyl,
3-chloro-4-[(4'-methylpiperazin-1'-yl)C(O)O-]benzyl,
3-chloro-4-[(4'-(pyridin-2-yl)piperazin-1'-yl)C(O)O-]benzyl,
3-chloro-4-[(thiomorpholin-4'-yl)C(O)O-]benzyl, and
3-fluoro-4-[(CH₃)₂NC(O)O-]benzyl.

In this embodiment, Ar is preferably aryl or substituted aryl and, even more preferably, is phenyl or substituted phenyl. Preferably, x is 1.

In another preferred embodiment, R¹ corresponds to the R⁶ group, (including the preferred embodiments) found in International Patent Application Publication No. WO 98/53817 which application is incorporated herein by reference in its entirety. In this embodiment, R¹ is preferably —CH₂—Ar²—Ar¹.

Preferably, R² is hydrogen. Preferably, R¹ and R² are derived from L-amino acids or other similarly configured starting materials. Alternatively, racemic mixtures can be used.

R³ is preferably hydrogen.

R⁴ is preferably hydrogen. When R⁴ is other than hydrogen, v is preferably 1 or 2.

Preferably, in the compounds of formula I above, X¹ is —C(O)₂Rᵈ. In the compounds of formula II, X² is preferably hydroxyl or alkoxy.

In the compound of formula II, Y is preferably hydrogen, —C(O)ORᵈ, —S(O)ₘRᵈ, —C(O)NRᵈRʰ, —NRᵈC(O)ORᵉ, —C(O)Rᵈ or —CH(OH)Rᵈ. When Y is —C(O)ORᵈ, R⁹ is preferably hydrogen or alkyl.

This invention also provides methods for binding VLA-4 in a biological sample which method comprises contacting the biological sample with a compound of formula I or II above under conditions wherein said compound binds to VLA-4.

Certain of the compounds of formula I and II above are also useful in reducing VLA-4 mediated inflammation in vivo.

This invention also provides pharmaceutical compositions comprising a pharmaceutically acceptable carrier and a therapeutically effective amount of one or more of the compounds of formula I or II above.

The pharmaceutical compositions may be used to treat VLA-4 mediated disease conditions. Such disease conditions include, by way of example, asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Other disease conditions include, but are not limited to, inflammatory conditions such as erythema nodosum, allergic conjunctivitis, optic neuritis, uveitis, allergic rhinitis, Ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

Accordingly, this invention also provides methods for the treatment of an inflammatory disease in a patient mediated by VLA-4 which methods comprise administering to the patient the pharmaceutical compositions described above.

Preferred compounds of this invention include those set forth in Table I below:

TABLE I

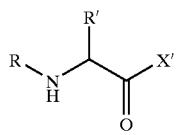

| Ex. No. | R | R' | X' |
|---|---|---|---|
| 1 | 3-methoxycarbonyl-adamant-1-yl-C(O)— | p-[(CH₃)₂NC(O)O-]benzyl- | —OH |
| 2 | 3-methoxycarbonyl-adamant-1-ylcarbonyl-C(O)— | p-[(CH₃)₂NC(O)O-]benzyl- | —OC(CH₃)₃ |
| 3 | adamant-1-yl-C(O)— | p-[(CH₃)₂NC(O)O-]benzyl- | —OC(CH₃)₃ |
| 4 | adamant-1-yl-C(O)— | p-[(CH₃)₂NC(O)O-]benzyl- | —OH |
| 5 | 3-N-methyl-N-benzyl-aminocarbonyladamant-1-yl-C(O)— | p-[(CH₃)₂NC(O)O-]benzyl- | —OC(CH₃)₃ |
| 6 | adamant-1-yl-C(O)— | p-[(1,1-dioxothiomorpholin-4-yl)C(O)O-]benzyl- | —OH |
| 7 | 3-N-methyl-N-benzyl-aminocarbonyladamant-1-yl-C(O)— | p-[(CH₃)₂NC(O)O-]benzyl- | —OH |

TABLE I-continued

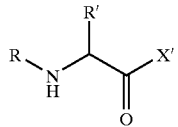

| Ex. No. | R | R' | X' |
|---|---|---|---|
| 8 | 3-methoxycarbonyl-adamant-1-yl-C(O)— | p-[(CH$_3$)$_2$NC(O)O-]benzyl- | —OC$_2$H$_5$ |
| 9 | 3-carboxyadamant-1-yl-C(O)— | p-[(CH$_3$)$_2$NC(O)O-]benzyl- | —OC(CH$_3$)$_3$ |
| 10 | 3-carboxyadamant-1-yl-C(O)— | p-[(CH$_3$)$_2$NC(O)O-]benzyl- | —OH |
| 11 | 3-tert-butoxycarbonyl-adamant-1-yl-C(O)— | p-[(CH$_3$)$_2$NC(O)O-]benzyl- | —OH |
| 12 | 3-(2-propoxy)carbonyl-adamant-1-yl-C(O)— | p-[(CH$_3$)$_2$NC(O)O-]benzyl- | —OH |
| 13 | 3-N-methylaminocarbonyl-adamant-1-yl-C(O)— | p-[(CH$_3$)$_2$NC(O)O-]benzyl- | —OH |
| 14 | 3-aminocarbonyladamant-1-yl-C(O)— | p-[(CH$_3$)$_2$NC(O)O-]benzyl- | —OH |
| 15 | 3-methylcarbonyladamant-1-yl-C(O)— | p-[(CH$_3$)$_2$NC(O)O-]benzyl- | —OH |
| 16 | 3-methoxycarbonylamino-adamant-1-yl-C(O)— | p-[(CH$_3$)$_2$NC(O)O-]benzyl- | —OCH$_3$ |
| 17 | 3-methylcarbonyladamant-1-yl-C(O)— | p-[(CH$_3$)$_2$NC(O)O-]benzyl- | —OCH$_3$ |
| 18 | 3-(1-hydroxyethyl)-adamant-1-yl-C(O)— | p-[(CH$_3$)$_2$NC(O)O-]benzyl- | —OH |
| 19 | 3-methoxycarbonyl-adamant-1-yl-C(O)— | p-[(piperazin-1-yl)C(O)O-]benzyl- | —OH |
| 20 | 3-methoxycarbonyl-adamant-1-yl-C(O)— | p-[(4-methylpiperazin-1-yl)C(O)O-]benzyl- | —OH |
| 21 | 3-methoxycarbonyl-adamant-1-yl-C(O)— | p-[(4-methylpiperazin-1-yl)C(O)O-]benzyl- | —OCH(CH$_3$)$_2$ |
| 22 | 3-methoxycarbonyl-adamant-1-yl-C(O)— | p-[(piperazin-1-yl)C(O)O-]benzyl- | —OCH(CH$_3$)$_2$ |
| 23 | 3-methoxycarbonyl-adamant-1-yl-C(O)— | p-[(4-methylpiperazin-1-yl)C(O)O-]benzyl- | —OC(CH$_3$)$_3$ |
| 24 | quinuclidin-2-yl-C(O)— | p-[(CH$_3$)$_2$NC(O)O-]benzyl- | —OH |
| 25 | 3-methoxycarbonyl-adamant-1-yl-C(O)— | p-[(1-methyl-2-pyridone-3-yl)C(O)O-]benzyl- | —O-benzyl |
| 26 | 3-methoxycarbonyl-adamant-1-yl-C(O)— | p-[(1-methyl-2-pyridone-3-yl)C(O)O-]benzyl- | —OH |
| 27 | 3-carboxyadamant-1-yl-C(O)— | 4-(2-NC—Ph-)benzyl- | —OH |
| 28 | 3-methoxycarbonyl-adamant-1-yl-C(O)— | 4-(2-CH$_3$O—Ph-)benzyl- | —OCH$_3$ |
| 29 | 3-methoxycarbonyl-adamant-1-yl-C(O)— | 4-(2-F—Ph-)benzyl- | —OCH$_3$ |
| 30 | 3-methoxycarbonyl-adamant-1-yl-C(O)— | 4-(1,3-dimethyl-2,4-dioxopyrimidin-5-yl)benzyl- | —OCH$_3$ |
| 31 | 3-methoxycarbonyl-adamant-1-yl-C(O)— | 4-(2,4-dimethoxypyrimidin-5-yl)benzyl- | —OCH$_3$ |
| 32 | 3-methoxycarbonyl-adamant-1-yl-C(O)— | 4-(2-pyridyl)benzyl- | —OCH$_3$ |
| 33 | 3-methoxycarbonyl-adamant-1-yl-C(O)— | 4-(1-oxo-2-pyridyl)benzyl- | —OCH$_3$ |
| 34 | 3-methoxycarbonyl-adamant-1-yl-C(O)— | 4-(1-oxo-2-pyridyl)benzyl- | —OH |
| 35 | 3-methoxycarbonyl-adamant-1-yl-C(O)— | 4-(1-methyl-2-oxo-3-pyridyl)-benzyl- | —OH |
| 36 | 3-methoxycarbonyl-adamant-1-yl-C(O)— | 4-(1-methyl-2-oxopiperidin-3'-yl)benzyl- | —OCH$_3$ |
| 37 | 3-methoxycarbonyl-adamant-1-yl-C(O)— | 4-[(CH$_3$)$_2$NC(O)CH$_2$-]benzyl- | —OH |
| 38 | 3-methioxycarbonyl-adamant-1-yl-C(O)— | 4-[(CH$_3$)$_2$NC(O)CF$_2$-]benzyl- | —OH |
| 39 | 3-methoxycarbonyl-adamant-1-yl-C(O)— | 4-[(CH$_3$)$_3$COC(O)]piperazin-1-yl-CH$_2$— | —OCH$_3$ |
| 40 | 3-methoxycarbonyl-adamant-1-yl-C(O)— | piperidin-1-yl-CH$_2$— | —OCH$_3$ |
| 41 | 3-methoxycarbonyl-adamant-1-yl-C(O)— | piperazin-1-yl-CH$_2$— | —OCH$_3$ |

TABLE I-continued $$R-\underset{H}{N}-\underset{\underset{O}{\|}}{C}-X'$$
(with R' on the α-carbon)

| Ex. No. | R | R' | X' |
|---|---|---|---|
| 42 | 3-methoxycarbonyl-adamant-1-yl-C(O)— | 4-[(CH₃)₂NC(O)CH₂—]-piperazin-1-yl-CH₂— | —OH |
| 43 | 3-methoxycarbonyl-adamant-1-yl-C(O)— | 4-[(CH₃)₂NC(O)O—]-cyclohex-1-yl-CH₂— | —OH |
| 44 | 3-methoxycarbonyl-adamant-1-yl-C(O)— | 4-[(CH₃)₂NC(O)CH═]-cyclohex-1-yl-CH₂— | —OH |
| 45 | 3-methoxycarbonyl-adamant-1-yl-C(O)— | (CH₃)₃COC(O)NH—(CH₂)₄— | —OCH₃ |
| 46 | 3-methoxycarbonyl-adamant-1-yl-C(O)— | (CH₃)₂NC(O)NH—(CH₂)₄— | —OCH₃ |
| 47 | 3-methoxycarbonyl-adamant-1-yl-C(O)— | (CH₃)₂NC(O)NH—(CH₂)₄— | —OH |
| 48 | 3-methoxycarbonyl-adamant-1-yl-C(O)— | (CH₃)₂NC(O)NH—(CH₂)₃— | —OH |
| 49 | 3-methoxycarbonyl-adamant-1-yl-C(O)— | H—C≡C—CH₂— | —OH |
| 50 | 3-methoxycarbonyl-adamant-1-yl-C(O)— | (CH₃)₂NC(O)—C≡C—CH₂— | —OH |
| 51 | 3-metboxycarbonyl-adamant-1-yl-C(O)— | (CH₃)₂NC(O)CH₂—C≡C—CH₂— | —OH |
| 52 | 3-methoxycarbonyl-adamant-1-yl-C(O)— | 3-(2-CH₃O—Ph-)isoxazol-5-yl- | —OH |
| 53 | 3-methoxycarbonyl-adamant-1-yl-C(O)— | 3-(2-NO₂—Ph-)isoxazol-5-yl- | —OH |
| 54 | 3-methoxycarbonyl-adamant-1-yl-C(O)— | 3-(2-NC—Ph-)isoxazol-5-yl- | —OH |
| 55 | 3-methoxycarbonyl-adamant-1-yl-C(O)— | (CH₃)₃OC(O)NHCH₂—C≡C—CH₂— | —OCH₃ |
| 56 | 3-methoxycarbonyl-adamant-1-yl-C(O)— | (CH₃)₂NC(O)NHCH₂—C≡C—CH₂— | —OCH₃ |
| 57 | 3-methoxycarbonyl-adamant-1-yl-C(O)— | (CH₃)₂NC(O)NHCH₂—C≡C—CH₂— | —OH |
| 58 | 3-N,N-dimethyl-aminocarbonyladamant-1-yl-C(O)— | p-[(CH₃)₂NC(O)O-]benzyl- | —OCH(CH₃)₂ |
| 59 | 3-N,N-dimethyl-aminocarbonyladamant-1-yl-C(O)— | p-[(CH₃)₂NC(O)O-]benzyl- | —OH |
| 60 | 3-[CH₃C(O)-]adamant-1-yl-C(O)— | p-[(CH₃)₂NC(O)O-]benzyl- | —OCH(CH₃)₂ |
| 61 | 3-[CH₃C(O)-]adamant-1-yl-C(O)— | p-[(CH₃)₂NC(O)O-]benzyl- | —OH |
| 62 | 3-(1-HO-eth-1-yl)adamant-1-yl-C(O)— | p-[(CH₃)₂NC(O)O-]benzyl- | —OCH(CH₃)₂ |
| 63 | 3-(1-HO-eth-1-yl)adamant-1-yl-C(O)— | p-[(CH₃)₂NC(O)O-]benzyl- | —OH |
| 64 | 3-methoxycarbonyl-adamant-1-yl-C(O)— | 4-[(CH₃)₂NC(O)CH═CH—]-benzyl- | —OCH₃ |
| 65 | 3-methoxycarbonyl-adamant-1-yl-C(O)— | 2-[(CH₃)₂NC(O)NH-]thiazol-4-yl-CH₂— | —OCH₃ |
| 66 | 3-methoxycarbonyl-adamant-1-yl-C(O)— | 2-[(CH₃)₂NC(O)NH-]thiazol-4-yl-CH₂— | —OH |
| 67 | 3-methoxycarbonyl-adamant-1-yl-C(O)— | 2-pyridyl-CH₂— | —OCH₃ |

Accordingly, this invention is also directed to each of the following compounds:

N-(adamant-1-ylcarbonyl)-L-4-(N,N-dimethylcarbamyloxy)phenylalanine tert-butyl ester, N-(adamant-1-ylcarbonyl)-L4-(N,N-dimethylcarbamyloxy)phenylalanine, N-(3-methoxycarbonyladamant-1-ylcarbonyl)-L-4-(N,N-dimethylcarbamyloxy)phenylalanine, N-(3-methoxycarbonyladamant-1-ylcarbonyl)-L-4-(N,N-dimethylcarbamyloxy)phenylalanine tert-butyl ester, N-[3-(N-benzyl-N-methylaminocarbonyl)adamant-1-ylcarbonyl]-L-4-(N,N-dimethylcarbamyloxy)phenylalanine tert-butyl ester, N-(adamant-1-ylcarbonyl)-L-4-(1,1-dioxothiomorpholin-4-ylcarbonyloxy)phenylalanine, N-[3-(N-benzyl-N-methylaminocarbonyl)adamant-1-ylcarbonyl]-L4-(N,N-dimethylcarbamyloxy)phenylalanine, N-(3-methoxycarbonyladamant-1-ylcarbonyl)-L4-(N,N-dimethylcarbamyloxy)phenylalanine ethyl ester, N-(3-carboxyadamant-1-ylcarbonyl)-L4-(N,N-dimethylcarbamyloxy)phenylalanine tert-butyl ester,
N-(3-carboxyadamant-1-ylcarbonyl)-L-4-(N,N-dimethylcarbamyloxy)phenylalanine,
N-(3-tert-butoxycarbonyladamant-1-ylcarbonyl)-L4-(N,N-dimethylcarbamyloxy)phenylalanine,
N-(3-isopropoxycarbonyladamant-1-ylcarbonyl)-L4-(N,N-dimethylcarbamyloxy)phenylalanine,
N-[3-(N-methylaminocarbonyl)adamant-1-ylcarbonyl]-L-4-(N,N-dimethylcarbamyloxy)phenylalanine,
N-[3-(aminocarbonyl)adamant-1-ylcarbonyl]]-L-4-(N,N-dimethylcarbamyloxy)phenylalanine,
N-(3-methylcarbonyladamant-1-ylcarbonyl)-L4-(N,N-dimethylcarbamyloxy)phenylalanine,
N-(3-methoxycarbonylaminoadamant-1-ylcarbonyl)-L4-(N,N-dimethylcarbamyloxy)phenylalanine,
N-(3-methylcarbonyladamant-1-ylcarbonyl)-L4-(N,N-dimethylcarbamyloxy)phenylalanine methyl ester,
N-[3-(1-hydroxyethyl)adamant-1-ylcarbonyl]-L4-(N,N-dimethylcarbamyloxy)phenylalanine,
N-(3-methoxycarbonyladamant-1-ylcarbonyl)-L4-(piperazin-1-ylcarbonyloxy)phenylalanine,
N-(3-methoxycarbonyladamant-1-ylcarbonyl)-L4-(4-methylpiperazin-1-ylcarbonyloxy)phenylalanine,
N-(3-methoxycarbonyladamant-1-ylcarbonyl)-L-4-(4-methylpiperazin-1-ylcarbonyloxy)phenylalanine isopropyl ester,
N-(3-methoxycarbonyladamant-1-ylcarbonyl)-L-4-(piperazin-1-ylcarbonyloxy)phenylalanine isopropyl ester,
N-(3-methoxycarbonyladamant-1-ylcarbonyl)-L-4-(4-methylpiperazin-1-ylcarbonyloxy)phenylalanine tert-butyl ester,
N-(quinuclidin-2-ylcarbonyl)-L-4-(N,N-dimethylcarbamyloxy)phenylalanine,
N-(3-methoxycarbonyladamant-1-ylcarbonyl)-L4-(1-methyl-2-pyridone-3-yl)phenylalanine benzyl ester,
N-(3-methoxycarbonyladamant-1-ylcarbonyl)-L4-(1-methyl-2-pyridone-3-yl)phenylalanine,
and pharmaceutically acceptable salts thereof.

DETAILED DESCRIPTION OF THE INVENTION

As above, this invention relates to compounds which inhibit leukocyte adhesion and, in particular, leukocyte adhesion mediated by VLA-4. However, prior to describing this invention in further detail, the following terms will first be defined.

Definitions

As used herein, "alkyl" refers to alkyl groups preferably having from 1 to 10 carbon atoms and more preferably 1 to 6 carbon atoms. This term is exemplified by groups such as methyl, t-butyl, n-heptyl, octyl and the like.

"Substituted alkyl" refers to an alkyl group, preferably of from 1 to 10 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono-and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkoxy" refers to the group "alkyl-O—" which includes, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Alkenoxy" refers to the group "alkenyl-O—".

"Substituted alkenoxy" refers to the group "substituted alkenyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)— cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 10 carbon atoms and more preferably 2 to 6 carbon atoms and having at least 1 and preferably from 1–2 sites of alkenyl unsaturation.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono-and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkynyl" refers to alkynyl group preferably having from 2 to 10 carbon atoms and more preferably 3 to 6 carbon atoms and having at least 1 and preferably from 1–2 sites of alkynyl unsaturation.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono-and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Amidino" refers to the group H$_2$NC(=NH)— and the term "alkylamidino" refers to compounds having 1 to 3 alkyl groups (e.g., alkylHNC(=NH)—).

"Thioamidino" refers to the group RSC(=NH)— where R is hydrogen or alkyl.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O) substituted alkenyl, —NRC(O)alkynyl, —NRC(O) substituted alkynyl, —NRC(O)aryl, —NRC(O)substituted aryl, —NRC(O)heteroaryl, —NRC(O)substituted heteroaryl, —NRC(O)heterocyclic, and —NRC(O) substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)NH$_2$, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH$_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like). Preferred aryls include phenyl and naphthyl.

Substituted aryl refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono-and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Aryloxy" refers to the group aryl-O— which includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono-and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclooctyl and the like. "Multicyclic bridged cycloalkyl" refers to cycloalkyl groups having two or more rings and one or more carbon bridging atoms. Examples of multicyclic bridged cycloalkyl groups include adamantyl and the like.

"Cycloalkenyl" refers to cyclic alkenyl groups of from 3 to 8 carbon atoms having single or multiple unsaturation but which are not aromatic. "Multicyclic bridged cycloalkenyl" refers to cycloalkenyl groups having two or more rings and one or more carbon bridging atoms.

"Substituted cycloalkyl" and "substituted cycloalkenyl" refer to a cycloalkyl and cycloalkenyl groups, preferably of from 3 to 8 carbon atoms, having from 1 to 5 substituents selected from the group consisting of oxo (═O), thioxo (═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono-and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Cycloalkoxy" refers to —O-cycloalkyl groups.

"Substituted cycloalkoxy" refers to —O-substituted cycloalkyl groups.

"Cycloalkenoxy" refers to —O-cycloalkenyl groups.

"Substituted cycloalkenoxy" refers to —O-substituted cycloalkenyl groups.

"Guanidino" refers to the groups —NRC(=NR)NRR, —NRC(=NR)NR-alkyl, —NRC(=NR)NR-substituted alkyl, —NRC(=NR)NR-alkenyl, —NRC(=NR)NR-substituted alkenyl, —NRC(=NR)NR-alkynyl, —NRC(=NR)NR-substituted alkynyl, —NRC(=NR)NR-aryl, —NRC(=NR)NR-substituted aryl, —NRC(=NR)NR-cycloalkyl, —NRC(=NR)NR-heteroaryl, —NRC(=NR)NR-substituted heteroaryl, —NRC(=NR)NR-heterocyclic, and —NRC(=NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Guanidinosulfone" refers to the groups —NRC(=NR)NRSO$_2$-alkyl, —NRC(=NR)NRSO$_2$-substituted alkyl, —NRC(=NR)NRSO$_2$-alkenyl, —NRC(=NR)NRSO$_2$-substituted alkenyl, —NRC(=NR)NRSO$_2$-alkynyl, —NRC(=NR)NRSO$_2$-substituted alkynyl, —NRC(=NR)NRSO$_2$-aryl, —NRC(=NR)NRSO$_2$-substituted aryl, —NRC(=NR)NRSO$_2$-cycloalkyl, —NRC(=NR)NRSO$_2$-substituted cycloalkyl, —NRC(=NR)NRSO$_2$-heteroaryl, and —NRC(=NR)NRSO$_2$-substituted heteroaryl, —NRC(=NR)NRSO$_2$-heterocyclic, and —NRC(=NR)NRSO$_2$-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or bromo.

"Heteroaryl" refers to an aromatic carbocyclic group of from 2 to 10 carbon atoms and 1 to 4 heteroatoms selected from oxygen, nitrogen and sulfur within the ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl and furyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heteroaryloxy" refers to the —O-heteroaryl and "substituted heteroaryloxy" refers to the —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from nitrogen, sulfur or oxygen within the ring wherein, in fused ring systems, one or more of the rings can be aryl or heteroaryl. "Multicyclic bridged hetereocyclic" refers to hetereocyclic groups having two or more rings and one or more bridging atoms. Examples of multicyclic bridged cycloalkyl groups include quinuclidinyl and the like.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono-and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuranyl, and the like.

"Heterocyclyloxy" refers to the —O-heterocyclic and "substituted heterocyclyloxy" refers to the —O-substituted heterocyclic.

"Lactam" refers to a ring containing the group —C(O)—NR— as part of the ring, where R is alkyl, substituted alkyl, aryl, substituted aryl, cycloalkyl, substituted cycloalkyl, heterocyclic, substituted heterocyclic, heteroaryl, substituted heteroaryl and —C(O)OR.

"Thiol" refers to the group —SH.

"Thioalkyl" refers to the groups —S-alkyl

"Substituted thioalkyl" refers to the group —S-substituted alkyl.

"Thiocycloalkyl" refers to the groups —S-cycloalkyl. "Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, N.Y., 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

In a preferred method of synthesis, the compounds of formula I are prepared by coupling a multicyclic bridged ring carboxylic acid derivative of formula III:

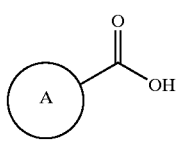

where ring A is as defined herein, with an amino acid derivative of formula IV:

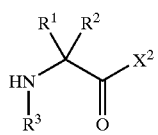

where $R^1$, $R^2$, $R^3$ and $X^2$ are as defined herein, under conventional amino acid coupling conditions. In some case, conventional protecting groups may be required to prevent undesired side reactions, such as where $X^2$ is hydroxyl. In such cases, esters, i.e., where $X^2$ is alkoxy, will typically be employed.

This coupling reaction is typically conducted using well-known coupling reagents such as carbodiimides, BOP reagent (benzotriazol-1-yloxy-tris(dimethylamino) phosphonium hexafluorophosphonate) and the like. Suitable carbodiimides include, by way of example, dicyclohexylcarbodiimide (DCC), 1-(3-dimethylaminopropyl)-3-ethylcarbodiimide (EDC) and the like. If desired, polymer supported forms of carbodiimide coupling reagents may also be used including, for example, those described in *Tetrahedron Letters*, 34(48), 7685 (1993). Additionally, well-known coupling promoters, such as N-hydroxysuccinimide, 1-hydroxybenzotriazole and the like, may be used to facilitate the coupling reaction.

This coupling reaction is typically conducted by contacting intermediate III with about 1 to about 2 equivalents of the coupling reagent and at least one equivalent, preferably about 1 to about 1.2 equivalents, of amino acid derivative IV in an inert diluent, such as dichloromethane, chloroform, acetonitrile, tetrahydrofuran, N,N-dimethylformamide and the like. Generally, this reaction is conducted at a temperature ranging from about 0° C. to about 37° C. for about 12 to about 24 hours. Upon completion of the reaction, the compound of formula IA is recovered by conventional methods including neutralization, extraction, precipitation, chromatography, filtration, and the like.

Alternatively, the intermediate III can be converted into an acid halide and the acid halide coupled with amino acid derivative IV to provide compounds of formula I. The acid halide of III can be prepared by contacting III with an inorganic acid halide, such as thionyl chloride, phosphorous trichloride, phosphorous tribromide or phosphorous pentachloride, or preferably, with oxalyl chloride under conventional conditions. Generally, this reaction is conducted using about 1 to 5 molar equivalents of the inorganic acid halide or oxalyl chloride, either neat or in an inert solvent, such as dichloromethane or carbon tetrachloride, at temperature in the range of about 0° C. to about 80° C. for about 1 to about 48 hours. A catalyst, such as N,N-dimethylformamide, may also be used in this reaction.

The acid halide of intermediate III is then contacted with at least one equivalent, preferably about 1.1 to about 1.5 equivalents, of amino acid derivative IV in an inert diluent, such as dichloromethane, at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like. Upon completion of the reaction, the compound of formula I is recovered by conventional methods including neutralization, extraction, precipitation, chromatography, filtration, and the like.

The multicyclic bridged ring compounds of formula III employed in the above described coupling reaction are either commercially available or can be prepared from commercially available starting materials using conventional procedures and reagents. Preferred multicyclic bridged ring compounds for use in this reaction include 1-adamantanecarboxylic acid derivatives and 2-quinuclidinecarboxylic acid derivatives.

The amino acid derivatives of formula IV employed in the above reactions are either known compounds or compounds that can be prepared from known compounds by conventional synthetic procedures. For example, amino acid derivatives of formula IV can be prepared by C-alkylating commercially available diethyl 2-acetamidomalonate (Aldrich, Milwaukee, Wis., USA) with an alkyl or substituted alkyl halide. This reaction is typically conducted by treating the diethyl 2-acetamidomalonate with at least one equivalent of sodium ethoxide and at least one equivalent of an alkyl or substituted alkyl halide in refluxing ethanol for about 6 to about 12 hours. The resulting C-alkylated malonate is then deacetylated, hydrolyzed and decarboxylated by heating in aqueous hydrochloric acid at reflux for about 6 to about 12 hours to provide the amino acid, typically as the hydrochloride salt.

Examples of amino acid derivatives of formula IV suitable for use in the above reactions include, but are not limited to, L-tyrosine methyl ester, L-3,5-diiodotyrosine methyl ester, L-3-iodotyrosine methyl ester, β-(4-hydroxynaphth-1-yl)-L-alanine methyl ester, β-(6-hydroxy-naphth-2-yl)-L-alanine methyl ester, L-4-(N,N-dimethylcarbamyloxy)phenylalanine ethyl ester and the like. If desired, of course, other esters or amides of the above-described compounds may also be employed.

For ease of synthesis, the compounds of formula I are typically prepared as an ester, i.e., where $X^2$ is an alkoxy or substituted alkoxy group and the like. If desired, the ester group can be hydrolysed using conventional conditions and reagents to provide the corresponding carboxylic acid. Typically, this reaction is conducted by treating the ester with at least one equivalent of an alkali metal hydroxide, such as lithium, sodium or potassium hydroxide, in an inert diluent, such as methanol or mixtures of methanol and water, at a temperature ranging about 0° C. to about 24° C. for about 1 to about 12 hours. Alternatively, benzyl esters may be removed by hydrogenolysis using a palladium catalyst, such as palladium on carbon. The resulting carboxylic acids may be coupled, if desired, to amines such as β-alanine ethyl ester, hydroxyamines such as hydroxylamine and N-hydroxysuccinimide, alkoxyamines and substituted alkoxyamines such as O-methylhydroxylamine and O-benzylhydroxylamine, and the like, using conventional coupling reagents and conditions as described above.

In another preferred method of synthesis, the multicyclic bridged ring carboxylic acid of formula III is coupled to a polymer-bound amino acid derivative of formula V:

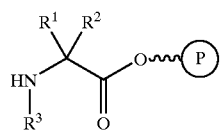

where $R^1$, $R^2$ and $R^3$ are as defined herein, and (p) represents a polymer or resin. Polymer-bound amino acids are commercially available or can be prepared by conventional procedures. Using the coupling procedures described above, compounds of formula I can be coupled to polymer-bound amino acid derivative V and then cleaved from the polymer to provide compounds of formula I. Methods for preparing, coupling and cleaving polymer-bound amino acids are well known. Such methods are described for example, in International Publication Number WO 98/53814, published Dec. 3, 1998, the disclosure of which is incorporated herein by reference in its entirety.

As will be apparent to those skilled in the art, other functional groups present on any of the substituents of the compounds of formula I or II, in addition to the carbamate-type functionality, can be readily modified or derivatized either before or after the above-described synthetic reactions using well-known synthetic procedures. For example, a nitro group present on a substituent of a compound of formula I or an intermediate thereof may be readily reduced by hydrogenation in the presence of a palladium catalyst, such as palladium on carbon, to provide the corresponding amino group. This reaction is typically conducted at a temperature of from about 20° C. to about 50° C. for about 6 to about 24 hours in an inert diluent, such as methanol. Compounds having a nitro group on the $R^3$ and/or $R^{3'}$ substituent can be prepared, for example, by using a 4-nitrophenylalanine derivative and the like in the above-described coupling reactions.

Similarly, a pyridyl group can be hydrogenated in the presence of a platinum catalyst, such as platinum oxide, in an acidic diluent to provide the corresponding piperidinyl analogue. Generally, this reaction is conducted by treating the pyridine compound with hydrogen at a pressure ranging from about 20 psi to about 60 psi, preferably about 40 psi, in the presence of the catalyst at a temperature of about 20° C. to about 50° C. for about 2 to about 24 hours in an acidic diluent, such as a mixture of methanol and aqueous hydrochloric acid.

Additionally, when the $R^1$ substituent of a compound of formula I or II or an intermediate thereof contains a primary or secondary amino group, such amino groups can be further derivatized either before or after the above coupling reactions to provide, by way of example, amides, sulfonamides, ureas, thioureas, carbamates, secondary or tertiary amines and the like. Compounds having a primary amino group on the $R^1$ substituent may be prepared, for example, by reduction of the corresponding nitro compound as described above.

By way of illustration, a compound of formula I or II or an intermediate thereof having a substituent containing a primary or secondary amino group, such as where $R^1$ is a (4-aminophenyl)methyl group, can be readily N-acylated using conventional acylating reagents and conditions to provide the corresponding amide. This acylation reaction is typically conducted by treating the amino compound with at least one equivalent, preferably about 1.1 to about 1.2 equivalents, of a carboxylic acid in the presence of a coupling reagent such as a carbodiimide, BOP reagent (benzotriazol-1-yloxy-tris(dimethylamino)phosphonium hexafluorophosphonate) and the like, in an inert diluent, such as dichloromethane, chloroform, acetonitrile, tetrahydrofuran, N,N-dimethylformamide and the like, at a temperature ranging from about 0° C. to about 37° C. for about 4 to about 24 hours. Preferably, a promoter, such as N-hydroxysuccinimide, 1-hydroxy-benzotriazole and the like, is used to facilitate the acylation reaction. Examples of carboxylic acids suitable for use in this reaction include, but are not limited to, N-tert-butyloxycarbonylglycine, N-tert-butyloxycarbonyl-L-phenylalanine, N-tert-butyloxycarbonyl-L-aspartic acid benzyl ester, benzoic acid, N-tert-butyloxycarbonylisonipecotic acid, N-methylisonipecotic acid, N-tert-butyloxycarbonylnipecotic acid, N-tert-butyloxycarbonyl-L-tetrahydroisoquinoline-3-carboxylic acid, N-(toluene-4-sulfonyl)-L-proline and the like.

Alternatively, a compound of formula I or II or an intermediate thereof containing a primary or secondary amino group can be N-acylated using an acyl halide or a carboxylic acid anhydride to form the corresponding amide. This reaction is typically conducted by contacting the amino compound with at least one equivalent, preferably about 1.1 to about 1.2 equivalents, of the acyl halide or carboxylic acid anhydride in an inert diluent, such as dichloromethane, at a temperature ranging from about of about −70° C. to about 40° C. for about 1 to about 24 hours. If desired, an acylation catalyst such as 4-(N,N-dimethylamino)pyridine may be used to promote the acylation reaction. The acylation reaction is preferably conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like.

Examples of acyl halides and carboxylic acid anhydrides suitable for use in this reaction include, but are not limited to, 2-methylpropionyl chloride, trimethylacetyl chloride, phenylacetyl chloride, benzoyl chloride, 2-bromobenzoyl chloride, 2-methylbenzoyl chloride, 2-trifluoro-methylbenzoyl chloride, isonicotinoyl chloride, nicotinoyl chloride, picolinoyl chloride, acetic anhydride, succinic anhydride, and the like. Carbamyl chlorides, such as N,N-dimethylcarbamyl chloride, N,N-diethylcarbamyl chloride and the like, can also be used in this reaction to provide ureas. Similarly, dicarbonates, such as di-tert-butyl dicarbonate, may be employed to provide carbamates.

In a similar manner, a compound of formula I or II or an intermediate thereof containing a primary or secondary amino group may be N-sulfonated to form a sulfonamide using a sulfonyl halide or a sulfonic acid anhydride. Sulfonyl halides and sulfonic acid anhydrides suitable for use in this reaction include, but are not limited to, methanesulfonyl chloride, chloromethanesulfonyl chloride, p-toluenesulfonyl chloride, trifluoromethanesulfonic anhydride, and the like. Similarly, sulfamoyl chlorides, such as dimethylsulfamoyl chloride, can be used to provide sulfamides (e.g., >N—SO$_2$—N<).

Additionally, a primary and secondary amino group present on a substituent of a compound of formula I or II or an intermediate thereof can be reacted with an isocyanate or a thioisocyanate to give a urea or thiourea, respectively. This reaction is typically conducted by contacting the amino compound with at least one equivalent, preferably about 1.1 to about 1.2 equivalents, of the isocyanate or thioisocyanate in an inert diluent, such as toluene and the like, at a temperature ranging from about 24° C. to about 37° C. for about 12 to about 24 hours. The isocyanates and thioisocyanates used in this reaction are commercially available or can be prepared from commercially available compounds using well-known synthetic procedures. For example, isocyanates and thioisocyanates are readily prepared by reacting the appropriate amine with phosgene or thiophosgene. Examples of isocyanates and thioisocyanates suitable for use in this reaction include, but are not limited to, ethyl isocyanate, n-propyl isocyanate, 4-cyanophenyl isocyanate, 3-methoxyphenyl isocyanate, 2-phenylethyl isocyanate, methyl thioisocyanate, ethyl thioisocyanate, 2-phenylethyl thioisocyanate, 3-phenylpropyl thioisocyanate, 3-(N,N-diethylamino)propyl thioisocyanate, phenyl thioisocyanate, benzyl thioisocyanate, 3-pyridyl thioisocyanate, fluorescein isothiocyanate (isomer I) and the like.

Furthermore, when a compound of formula I or II or an intermediate thereof contains a primary or secondary amino group, the amino group can be reductively alkylated using aldehydes or ketones to form a secondary or tertiary amino group. This reaction is typically conducted by contacting the amino compound with at least one equivalent, preferably about 1.1 to about 1.5 equivalents, of an aldehyde or ketone and at least one equivalent based on the amino compound of a metal hydride reducing agent, such as sodium cyanoborohydride, in an inert diluent, such as methanol, tetrahydrofuran, mixtures thereof and the like, at a temperature ranging from about 0° C. to about 50° C. for about 1 to about 72 hours. Aldehydes and ketones suitable for use in this reaction include, by way of example, benzaldehyde, 4-chlorobenzaldehyde, valeraldehyde and the like.

In a similar manner, when a compound of formula I or II or an intermediate thereof has a substituent containing a hydroxyl group, the hydroxyl group can be further modified or derivatized either before or after the above coupling reactions to provide, by way of example, ethers, carbamates and the like. Compounds having a hydroxyl group on the R$^1$ substituent, for example, can be prepared using an amino acid derivative derived from tyrosine and the like in the above-described reactions.

By way of example, a compound of formula I or II or an intermediate thereof having a substituent containing a hydroxyl group, such as where R$^1$ is a (4-hydroxyphenyl) methyl group, can be readily O-alkylated to form ethers. This O-alkylation reaction is typically conducted by contacting the hydroxy compound with a suitable alkali or alkaline earth metal base, such as potassium carbonate, in an inert diluent, such as acetone, 2-butanone and the like, to form the alkali or alkaline earth metal salt of the hydroxyl group. This salt is generally not isolated, but is reacted in situ with at least one equivalent of an alkyl or substituted alkyl halide or sulfonate, such as an alkyl chloride, bromide, iodide, mesylate or tosylate, to afford the ether. Generally, this reaction is conducted at a temperature ranging from about 60° C. to about 150° C. for about 24 to about 72 hours. Preferably, a catalytic amount of sodium or potassium iodide is added to the reaction mixture when an alkyl chloride or bromide is employed in the reaction.

Examples of alkyl or substituted alkyl halides and sulfonates suitable for use in this reaction include, but are not limited to, tert-butyl bromoacetate, N-tert-butyl chloroacetamide, 1-bromoethylbenzene, ethyl α-bromophenylacetate, 2-(N-ethyl-N-phenylamino)ethyl chloride, 2-(N,N-ethylamino)ethyl chloride, 2-(N,N-diisopropylamino)ethyl chloride, 2-(N,N-dibenzylamino) ethyl chloride, 3-(N,N-ethylamino)propyl chloride, 3-(N-benzyl-N-methylamino)propyl chloride, N-(2-chloroethyl) morpholine, 2-(hexamethyleneimino)ethyl chloride, 3-(N-methylpiperazine)propyl chloride, 1-(3-chlorophenyl)-4-(3-chloropropyl)piperazine, 2-(4-hydroxy-4-phenylpiperidine) ethyl chloride, N-tert-butyloxycarbonyl-3-piperidinemethyl tosylate, and the like.

Alternatively, a hydroxyl group present on a substituent of a compound of formula I or II or an intermediate thereof can be O-alkylating using the Mitsunobu reaction. In this reaction, an alcohol, such as 3-(N,N-dimethylamino)-1-propanol and the like, is reacted with about 1.0 to about 1.3 equivalents of triphenylphosphine and about 1.0 to about 1.3 equivalents of diethyl azodicarboxylate in an inert diluent, such as tetrahydrofuran, at a temperature ranging from about −10° C. to about 5° C. for about 0.25 to about 1 hour. About 1.0 to about 1.3 equivalents of a hydroxy compound, such as N-tert-butyltyrosine methyl ester, is then added and the reaction mixture is stirred at a temperature of about 0° C. to about 30° C. for about 2 to about 48 hours to provide the O-alkylated product.

In a similar manner, a compound of formula I or II or an intermediate thereof containing an aryl hydroxy group can be reacted with an aryl iodide to provide a diaryl ether. Generally, this reaction is conducted by forming the alkali metal salt of the hydroxyl group using a suitable base, such as sodium hydride, in an inert diluent such as xylenes at a temperature of about −25° C. to about 10° C. The salt is then treated with about 1.1 to about 1.5 equivalents of cuprous bromide dimethyl sulfide complex at a temperature ranging from about 10° C. to about 30° C. for about 0.5 to about 2.0 hours, followed by about 1.1 to about 1.5 equivalents of an aryl iodide, such as sodium 2-iodobenzoate and the like. The reaction is then heated to about 70° C. to about 150° C. for about 2 to about 24 hours to provide the diaryl ether.

Additionally, a hydroxy-containing compound can also be readily derivatized to form a carbamate. In one method for preparing such carbamates, a hydroxy compound of formula I or II or an intermediate thereof is contacted with about 1.0 to about 1.2 equivalents of 4-nitrophenyl chloroformate in an inert diluent, such as dichloromethane, at a temperature ranging from about −25° C. to about 0° C. for about 0.5 to about 2.0 hours. Treatment of the resulting carbonate with an excess, preferably about 2 to about 5 equivalents, of a trialkylamine, such as triethylamine, for about 0.5 to 2 hours, followed by about 1.0 to about 1.5 equivalents of a primary or secondary amine provides the carbamate. Examples of amines suitable for using in this reaction include, but are not limited to, piperazine, 1-methylpiperazine, 1-acetylpiperazine, morpholine, thiomorpholine, pyrrolidine, piperidine and the like.

Alternatively, in another method for preparing carbamates, a hydroxy-containing compound is contacted with about 1.0 to about 1.5 equivalents of a carbamyl chloride in an inert diluent, such as dichloromethane, at a temperature ranging from about 25° C. to about 70° C. for about 2 to about 72 hours. Typically, this reaction is conducted in the presence of a suitable base to scavenge the acid generated during the reaction. Suitable bases include, by way of example, tertiary amines, such as triethylamine, diisopropylethylamine, N-methylmorpholine and the like. Additionally, at least one equivalent (based on the hydroxy compound) of 4-(N,N-dimethylamino)pyridine is preferably added to the reaction mixture to facilitate the reaction. Examples of carbamyl chlorides suitable for use in this reaction include, by way of example, dimethylcarbamyl chloride, diethylcarbamyl chloride and the like.

Likewise, when a compound of formula I or II or an intermediate thereof contains a primary or secondary hydroxyl group, such hydroxyl groups can be readily converted into a leaving group and displaced to form, for example, amines, sulfides and fluorides. Generally, when a chiral compound is employed in these reactions, the stereochemistry at the carbon atom attached to the derivatized hydroxyl group is typically inverted.

These reactions are typically conducted by first converting the hydroxyl group into a leaving group, such as a tosylate, by treatment of the hydroxy compound with at least one equivalent of a sulfonyl halide, such as p-toluenesulfonyl chloride and the like, in pyridine. This reaction is generally conducted at a temperature of from about 0° C. to about 70° C. for about 1 to about 48 hours. The resulting tosylate can then be readily displaced with sodium azide, for example, by contacting the tosylate with at least one equivalent of sodium azide in an inert diluent, such as a mixture of N,N-dimethylformamide and water, at a temperature ranging from about 0° C. to about 37° C. for about 1 to about 12 hours to provide the corresponding azido compound. The azido group can then be reduced by, for example, hydrogenation using a palladium on carbon catalyst to provide the amino ($—NH_2$) compound.

Similarly, a tosylate group can be readily displaced by a thiol to form a sulfide. This reaction is typically conducted by contacting the tosylate with at least one equivalent of a thiol, such as thiophenol, in the presence of a suitable base, such as 1,8-diazabicyclo[5.4.0]undec-7-ene (DBU), in an inert diluent, such as N,N-dimethylformamide, at a temperature of from about 0° C. to about 37° C. for about 1 to about 12 hours to provide the sulfide. Additionally, treatment of a tosylate with morpholinosulfur trifluoride in an inert diluent, such as dichloromethane, at a temperature ranging from about 0° C. to about 37° C. for about 12 to about 24 hours affords the corresponding fluoro compound.

Furthermore, a compound of formula I or II or an intermediate thereof having a substituent containing an iodoaryl group, for example, when $R^1$ is a (4-iodophenyl)methyl group, can be readily converted either before or after the above coupling reactions into a biaryl compound. Typically, this reaction is conducted by treating the iodoaryl compound with about 1.1 to about 2 equivalents of an arylzinc iodide, such as 2-(methoxycarbonyl)phenylzinc iodide, in the presence of a palladium catalyst, such as palladium tetra (triphenylphosphine), in an inert diluent, such as tetrahydrofuran, at a temperature ranging from about 24° C. to about 30° C. until reaction completion. This reaction is further described, for example, in Rieke, *J. Org. Chem.* 1991, 56, 1445. Additional methods for preparing biaryl derivatives are disclosed in International Publication Number WO 98/53817, published Dec. 3, 1998, the disclosure of which is incorporated herein by reference in its entirety.

In some cases, the compounds of formula I or II or intermediates thereof may contain substituents having one or more sulfur atoms. When present, such sulfur atoms can be oxidized either before or after the above coupling reactions to provide a sulfoxide or sulfone compound using conventional reagents and reaction conditions. Suitable reagents for oxidizing a sulfide compound to a sulfoxide include, by way of example, hydrogen peroxide, 3-chloroperoxybenzoic acid (MCPBA), sodium periodate and the like. The oxidation reaction is typically conducted by contacting the sulfide compound with about 0.95 to about 1.1 equivalents of the oxidizing reagent in an inert diluent, such as dichloromethane, at a temperature ranging from about −50° C. to about 75° C. for about 1 to about 24 hours. The resulting sulfoxide can then be further oxidized to the corresponding sulfone by contacting the sulfoxide with at least one additional equivalent of an oxidizing reagent, such as hydrogen peroxide, MCPBA, potassium permanganate and the like. Alternatively, the sulfone can be prepared directly by contacting the sulfide with at least two equivalents, and preferably an excess, of the oxidizing reagent. Such reactions are described further in March, *"Advanced Organic Chemistry"*, 4th Ed., pp. 1201–1202, Wiley Publisher, 1992.

Other procedures and reaction conditions for preparing the compounds of this invention are described in the examples set forth below.

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I or II above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |

-continued

| Ingredient | Quantity (mg/tablet) |
|---|---|
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Formulation Example 9

An intravenous formulation may be prepared as follows:

| Ingredient | Quantity |
|---|---|
| Active Ingredient | 250.0 mg |
| Isotonic saline | 1000 ml |

Formulation Example 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Utility

The compounds of this invention can be employed to bind VLA-4 ($\alpha_4\beta_1$ integrin) in biological samples and, accordingly have utility in, for example, assaying such samples for VLA-4. In such assays, the compounds can be bound to a solid support and the VLA-4 sample added thereto. The amount of VLA-4 in the sample can be determined by conventional methods such as use of a sandwich ELISA assay. Alternatively, labeled VLA-4 can be used in a competitive assay to measure for the presence of VLA-4 in the sample. Other suitable assays are well known in the art.

In addition, certain of the compounds of this invention inhibit, in vivo, adhesion of leukocytes to endothelial cells mediated by VLA-4 and, accordingly, can be used in the treatment of diseases mediated by VLA-4. Such diseases include inflammatory diseases in mammalian patients such as asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

The biological activity of the compounds identified above may be assayed in a variety of systems. For example, a compound can be immobilized on a solid surface and adhesion of cells expressing VLA-4 can be measured. Using such formats, large numbers of compounds can be screened. Cells suitable for this assay include any leukocytes known to express VLA-4 such as T cells, B cells, monocytes, eosinophils, and basophils. A number of leukocyte cell lines can also be used, examples include Jurkat and U937.

The test compounds can also be tested for the ability to competitively inhibit binding between VLA-4 and VCAM-1, or between VLA-4 and a labeled compound known to bind VLA-4 such as a compound of this invention or antibodies to VLA-4. In these assays, the VCAM-1 can be immobilized on a solid surface. VCAM-1 may also be expressed as a recombinant fusion protein having an Ig tail (e.g., IgG) so that binding to VLA-4 may be detected in an immunoassay. Alternatively, VCAM-1 expressing cells, such as activated endothelial cells or VCAM-1 transfected fibroblasts can be used. For assays to measure the ability to block adhesion to brain endothelial cells, the assays described in International Patent Application Publication No. WO 91/05038 are particularly preferred. This application is incorporated herein by reference in its entirety.

Many assay formats employ labelled assay components. The labelling systems can be in a variety of forms. The label may be coupled directly or indirectly to the desired component of the assay according to methods well known in the art. A wide variety of labels may be used. The component may be labelled by any one of several methods. The most common method of detection is the use of autoradiography with $^3H$, $^{125}I$, $^{35}S$, $^{14}C$, or $^{32}P$ labelled compounds or the like. Non-radioactive labels include ligands which bind to labelled antibodies, fluorophores, chemiluminescent agents, enzymes and antibodies which can serve as specific binding pair members for a labelled ligand. The choice of label depends on sensitivity required, ease of conjugation with the compound, stability requirements, and available instrumentation.

Appropriate in vivo models for demonstrating efficacy in treating inflammatory responses include EAE (experimental autoimmune encephalomyelitis) in mice, rats, guinea pigs or primates, as well as other inflammatory models dependent upon $\alpha 4$ integrins.

Compounds having the desired biological activity may be modified as necessary to provide desired properties such as improved pharmacological properties (e.g., in vivo stability, bio-availability), or the ability to be detected in diagnostic applications. For instance, inclusion of one or more D-amino acids in the sulfonamides of this invention typically increases in vivo stability. Stability can be assayed in a variety of ways such as by measuring the half-life of the proteins during incubation with peptidases or human plasma or serum. A number of such protein stability assays have been described (see, e.g., Verhoef et al., Eur. J. Drug Metab. Pharmacokinet., 1990, 15(2:83–93).

For diagnostic purposes, a wide variety of labels may be linked to the compounds, which may provide, directly or indirectly, a detectable signal. Thus, the compounds of the subject invention may be modified in a variety of ways for a variety of end purposes while still retaining biological activity. In addition, various reactive sites may be introduced at the terminus for linking to particles, solid substrates, macromolecules, or the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

In vitro uses include diagnostic applications such as monitoring inflammatory responses by detecting the presence of leukocytes expressing VLA-4. The compounds of this invention can also be used for isolating or labeling such cells. In addition, as mentioned above, the compounds of the invention can be used to assay for potential inhibitors of VLA-4/VCAM-1 interactions.

For in vivo diagnostic imaging to identify, e.g., sites of inflammation, radioisotopes are typically used in accordance with well known techniques. The radioisotopes may be bound to the peptide either directly or indirectly using intermediate functional groups. For instance, chelating agents such as diethylenetriaminepentacetic acid (DTPA) and ethylenediaminetetraacetic acid (EDTA) and similar molecules have been used to bind proteins to metallic ion radioisotopes.

The complexes can also be labeled with a paramagnetic isotope for purposes of in vivo diagnosis, as in magnetic resonance imaging (MRI) or electron spin resonance (ESR), both of which are well known. In general, any conventional method for visualizing diagnostic imaging can be used. Usually gamma- and positron-emitting radioisotopes are used for camera imaging and paramagnetic isotopes are used for MRI. Thus, the compounds can be used to monitor the course of amelioration of an inflammatory response in an individual. By measuring the increase or decrease in lymphocytes expressing VLA-4 it is possible to determine whether a particular therapeutic regimen aimed at ameliorating the disease is effective.

The pharmaceutical compositions of the present invention can be used to block or inhibit cellular adhesion associated with a number of diseases and disorders. For instance, a number of inflammatory disorders are associated with integrins or leukocytes. Treatable disorders include, e.g., transplantation rejection (e.g., allograft rejection), Alzheimer's disease, atherosclerosis, AIDS dementia, diabetes (including acute juvenile onset diabetes), retinitis, cancer metastases, rheumatoid arthritis, acute leukocyte-mediated lung injury (e.g., adult respiratory distress syndrome), asthma, nephritis, and acute and chronic inflammation, including atopic dermatitis, psoriasis, myocardial ischemia, and inflammatory bowel disease (including Crohn's disease and ulcerative colitis). In preferred embodiments the pharmaceutical compositions are used to treat inflammatory brain disorders, such as multiple sclerosis (MS), viral meningitis and encephalitis.

Inflammatory bowel disease is a collective term for two similar diseases referred to as Crohn's disease and ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, *Immunology* (3d ed., Raven Press, 1993).

Another indication for the compounds of this invention is in treatment of organ or graft rejection mediated by VLA-4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. CD8$^+$ cells, CD4 cells and monocytes are all involved in the rejection of transplant tissues. Compounds of this invention which bind to alpha-4 integrin are useful, inter alia, to block alloantigen-induced immune responses in the donee thereby preventing such cells from participating in the destruction of the transplanted tissue or organ. See, e.g., Paul et al., *Transplant International* 9, 420–425 (1996); Georczynski et al., *Immunology* 87, 573–580 (1996); Georcyznski et al., *Transplant. Immunol.* 3, 55–61 (1995); Yang et al., *Transplantation* 60, 71–76 (1995); Anderson et al., *APMIS* 102, 23–27 (1994).

A related use for compounds of this invention which bind to VLA-4 is in modulating the immune response involved in "graft versus host" disease (GVHD). See e.g., Schlegel et al., *J. Immunol.* 155, 3856–3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

A further use of the compounds of this invention is inhibiting tumor metastasis. Several tumor cells have been reported to express VLA-4 and compounds which bind VLA-4 block adhesion of such cells to endothelial cells. Steinback et al., *Urol. Res.* 23, 175–83 (1995); Orosz et al., *Int. J. Cancer* 60, 867–71 (1995); Freedman et al., *Leuk. Lymphoma* 13, 47–52 (1994); Okahara et al., *Cancer Res.* 54, 3233–6 (1994).

A further use of the compounds of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against VLA-4 have been shown to block the adhesion of leukocytes to the endothelium, and thus prevent inflammation of the central nervous system and subsequent paralysis in the animals[16].

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985).

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 µg to about 500 µg per kilogram body weight, preferably about 100 µg to about 300 µg per kilogram body weight. Suitable dosage ranges for intranasal administration are generally about 0.1 pg to 1 mg per kilogram body weight. Effective doses can be extrapolated from dose-response curves derived from in vitro or animal model test systems.

Compounds of this invention are also capable of binding or antagonizing the actions of $\alpha_6\beta_1$, $\alpha_9\beta_1$, $\alpha_4\beta_7$, $\alpha_d\beta_2$, $\alpha_e\beta_7$ integrins (although $\alpha_4\beta_1$ and $\alpha_9\beta_1$ are preferred in this invention). Accordingly, compounds of this invention are also useful for preventing or reversing the symptoms, disorders or diseases induced by the binding of these integrins to their respective ligands.

For example, International Publication Number WO 98/53817, published Dec. 3, 1998 (the disclosure of which is incorporated herein by reference in its entirety) and references cited therein describe disorders mediated by $\alpha_4\beta_7$. This reference also describes an assay for determining antagonism of $\alpha_4\beta_7$ dependent binding to VCAM-Ig fusion protein.

Additionally, compounds that bind $\alpha_d\beta_2$ and $\alpha_e\beta_7$ integrins are particularly useful for the treatment of asthma and related lung diseases. See, for example, M. H. Grayson et al., *J. Exp. Med.* 1998, 188(11) 2187–2191. Compounds that bind $\alpha_e\beta_7$ integrin are also useful for the treatment of systemic lupus erythematosus (see, for example, M. Pang et al., *Arthritis Rheum.* 1998, 41(8), 1456–1463); Crohn's disease, ulcerative colitis and infammatory bowel disease (IBD) (see, for example, D. Elewaut et al., *Scand J. Gastroenterol* 1998, 33(7) 743–748); Sjogren's syndrome (see, for example, U. Kroneld et al., *Scand J. Gastroenterol* 1998, 27(3), 215–218); and rheumatoid arthritis (see, for example, *Scand J. Gastroenterol* 1996, 44(3), 293–298). And compounds that bind $\alpha_6\beta_1$ may be useful in preventing fertilization (see, for example, H. Chen et al., *Chem. Biol.* 1999, 6, 1–10).

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | | |
|---|---|---|
| aq or aq. | = | aqueous |
| AcOH | = | acetic acid |
| bd | = | broad doublet |
| bm | = | broad multiplet |
| bs | = | broad singlet |
| Bn | = | benzyl |
| Boc | = | N-tert-butoxylcarbonyl |
| Boc$_2$O | = | di-tert-butyl dicarbonate |
| BOP | = | benzotriazol-1-yloxy-tris(dimethylamino)phosphonium hexafluorophosphate |
| Cbz | = | carbobenzyloxy |
| CHCl$_3$ | = | chloroform |
| CH$_2$Cl$_2$ | = | dichloromethane |
| (COCl)$_2$ | = | oxalyl chloride |
| d | = | doublet |
| dd | = | doublet of doublets |
| dt | = | doublet of triplets |
| DBU | = | 1,8-diazabicyclo[5.4.0]undec-7-ene |
| DCC | = | 1,3-dicyclohexylcarbodiimide |
| DMAP | = | 4-N,N-dimethylaminopyridine |
| DME | = | ethylene glycol dimethyl ether |
| DMF | = | N,N-dimethylformamide |
| DMSO | = | dimethylsulfoxide |
| EDC | = | 1-(3-dimethylaminopropyl)-3-ethylcarbodiimide hydrochloride |
| Et$_3$N | = | triethylamine |
| Et$_2$O | = | diethyl ether |
| EtOAc | = | ethyl acetate |
| EtOH | = | ethanol |
| eq or eq. | = | equivalent |
| Fmoc | = | N-(9-fluorenylmethoxycarbonyl) |
| FmocONSu | = | N-(9-fluorenylmethoxycarbonyl)-succinimide |
| g | = | grams |
| h | = | hour |
| H$_2$O | = | water |
| HBr | = | hydrobromic acid |

-continued

| | | |
|---|---|---|
| HCl | = | hydrochloric acid |
| HOBT | = | 1-hydroxybenzotriazole hydrate |
| hr | = | hour |
| $K_2CO_3$ | = | potassium carbonate |
| L | = | liter |
| m | = | multiplet |
| MeOH | = | methanol |
| mg | = | milligram |
| $MgSO_4$ | = | magnesium sulfate |
| mL | = | milliliter |
| mm | = | millimeter |
| mM | = | millimolar |
| mmol | = | millimol |
| mp | = | melting point |
| N | = | normal |
| NaCl | = | sodium chloride |
| $Na_2CO_3$ | = | sodium carbonate |
| $NaHCO_3$ | = | sodium bicarbonate |
| NaOEt | = | sodium ethoxide |
| NaOH | = | sodium hydroxide |
| $NH_4Cl$ | = | ammonium chloride |
| NMM | = | N-methylmorpholine |
| Phe | = | L-phenylalanine |
| Pro | = | L-proline |
| psi | = | pounds per square inch |
| $PtO_2$ | = | platinum oxide |
| q | = | quartet |
| quint. | = | quintet |
| rt | = | room temperature |
| s | = | singlet |
| sat | = | saturated |
| t | = | triplet |
| t-BuOH | = | tert-butanol |
| TFA | = | trifluoroacetic acid |
| THF | = | tetrahydrofuran |
| TLC or tlc | = | thin layer chromatography |
| Ts | = | tosyl |
| TsCl | = | tosyl chloride |
| TsOH | = | tosylate |
| μL | = | microliter |

The following Methods may be used to prepare the compounds of this invention.

Method A

Methyl Ester Preparation Procedure

Amino acid methyl esters can be prepared using the method of Brenner and Huber *Helv. Chim. Acta* 1953, 36, 1109.

Method B

BOP Coupling Procedure

The desired dipeptide ester was prepared by the reaction of a carboxylic acid (1 equivalent) with the appropriate amino acid ester or amino acid ester hydrochloride (1 equivalent), benzotriazol-1-yloxy-tris(dimethylamino) phosphonium hexafluorophosphate [BOP] (2.0 equivalent), triethylamine (1.1 equivalent), and DMF. The reaction mixture was stirred at room temperature overnight. The crude product is purified flash chromatography to afford the dipeptide ester.

Method C

Hydrogenation Procedure I

Hydrogenation was performed using 10% palladium on carbon (10% by weight) in methanol at 30 psi overnight. The mixture was filtered through a pad of Celite and the filtrate concentrated to yield the desired compound.

Method D

Hydrolysis Procedure I

To a chilled (0° C.) THF/$H_2O$ solution (2:1, 5–10 mL) of the appropriate ester was added LiOH (or NaOH) (0.95 equivalents). The temperature was maintained at 0° C. and the reaction was complete in 1–3 hours. The reaction mixture was extracted with ethyl acetate and the aqueous phase was lyophilized resulting in the desired carboxylate salt.

Method E

Ester Hydrolysis Procedure II

To a chilled (0° C.) THF/$H_2O$ solution (2:1, 5–10 mL) of the appropriate ester was added LiOH (1.1 equivalents). The temperature was maintained at 0° C. and the reaction was complete in 1–3 hours. The reaction mixture was concentrated and the residue was taken up into $H_2O$ and the pH adjusted to 2–3 with aqueous HCl. The product was extracted with ethyl acetate and the combined organic phase was washed with brine, dried over $MgSO_4$, filtered and concentrated to yield the desired acid.

Method F

Ester Hydrolysis Procedure III

The appropriate ester was dissolved in dioxane/$H_2O$ (1:1) and 0.9 equivalents of 0.5 N NaOH was added. The reaction was stirred for 3–16 hours and then concentrated. The resulting residue was dissolved in $H_2O$ and extracted with ethyl acetate. The aqueous phase was lyophilized to yield the desired carboxylate sodium salt.

Method G

BOC Removal Procedure

Anhydrous hydrochloride (HCl) gas was bubbled through a methanolic solution of the appropriate Boc-amino acid ester at 0° C. for 15 minutes and the reaction mixture was stirred for three hours. The solution was concentrated to a syrup and dissolved in $Et_2O$ and reconcentrated. This procedure was repeated and the resulting solid was placed under high vacuum overnight.

Method H tert-Butyl Ester Hydrolysis Procedure I

The tert-butyl ester was dissolved in $CH_2Cl_2$ and treated with TFA. The reaction was complete in 1–3 hr at which time the reaction mixture was concentrated and the residue dissolved in $H_2O$ and lyophilized to yield the desired acid.

Method I

EDC Coupling Procedure I

To a $CH_2Cl_2$ solution (5–20 mL) of a carboxylic acid (1 equivalent), the appropriate amino acid ester hydrochloride (1 equivalent), N-methylmorpholine (1.1–2.2 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was poured into $H_2O$ and the organic phase was washed with sat. $NaHCO_3$, brine, dried ($MgSO_4$ or $Na_2SO_4$), filtered and concentrated. The crude product was purified by column chromatography.

Method J

EDC Coupling Procedure II

To a DMF solution (5–20 mL) of a carboxylic acid (1 equivalent), the appropriated amino acid ester hydrochloride (1 equivalent), $Et_3N$ (1.1 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was partitioned between EtOAc and $H_2O$ and the organic phase washed with 0.2 N citric acid, $H_2O$, sat. $NaHCO_3$, brine, dried ($MgSO_4$ or $Na_2SO_4$), filtered and concentrated. The crude product was purified by column chromatography or preparative TLC.

Method K tert-Butyl Ester Hydrolysis Procedure II

The tert-butyl ester was dissolved in $CH_2Cl_2$ (5 mL) and treated with TFA (5 mL). The reaction was complete in 1–3 hours at which time the reaction mixture was concentrated and the residue dissolved in $H_2O$ and concentrated. The residue was redissolved in $H_2O$ and lyophilized to yield the desired product.

Method L

Carbamate Formation Procedure I

Into a reaction vial were combined 15.2 mmol, 1.0 eq. of the starting hydroxy compound (typically a tyrosine derivative) and 1.86 g (15.2 mmol, 1.0 eq) DMAP. Methylene chloride (50 mL), triethylamine (2.12 mL, 1.54 g, 15.2 mmol, 1.0 eq), and dimethylcarbamyl chloride (1.68 mL, 1.96 g, 18.2 mmol, 1.2 eq) were then added. The vial was capped tightly, and the reaction solution swirled to obtain a homogeneous solution. The reaction solution was then heated to 40° C. After 48 h, TLC of the resulting colorless solution indicated complete conversion. The work-up of the reaction solution was as follows: 50 mL EtOAc and 50 mL hexanes was added to the reaction mixture, and the resulting mixture was washed with 0.5 M citric acid (3×50 mL), water (2×50 mL), 10% $K_2CO_3$ (2×50 mL), and sat. NaCl (1×50 mL); dried with $MgSO_4$, filtered and evaporated to afford the desired compound.

Method M

Carbamate Formation Procedure II

Into a reaction vial were combined 84.34 mmol (1.0 eq) of the starting hydroxy compound (typically a tyrosine derivative) and 17.0 g (84.34 mmol, 1.0 eq) 4-nitrophenyl chloroformate. Methylene chloride (700 mL) was added and the vial was capped with a septum. A nitrogen line was attached and the vial was immersed in a 4:1 water/ethanol dry ice slurry with stirring to cool to −15° C. Triethylamine (29.38 mL, 21.33 g, 210.81 mmol, 2.5 eq) was added over five minutes with stirring and the stirring was continued at −10 to −15° C. for 1 h. N-Methyl piperazine (9.35 mL, 8.45 g, 84.34 mmol, 1.0 eq) was added over three minutes with stirring and stirring was continued overnight while warming to room temperature. The reaction mixture was diluted with 700 mL hexanes and the resulting mixture was washed repeatedly with 10% $K_2CO_3$, until no yellow color (from 4-nitrophenol) is observed in the aqueous layer. The mixture was then washed with sat. NaCl, dried over anhydrous $MgSO_4$, filtered and evaporated. The residue was dissolved in 500 mL of ethanol and evaporated to remove triethylamine. The residue was again dissolved in 500 mL of ethanol and evaporated to remove triethylamine. The residue was then dissolved in 400 mL of ethanol and 600 mL of water was added with stirring to precipitate a solid or oil. If an oil if formed, the oil is stirred vigorously to induce it to solidify. The solid is then isolated by filtration. Dissolution, precipitation, and filtration are repeated once and the resulting solid is rinsed with water to remove traces of yellow color. The solid is then subjected to high vacuum until the mass remains constant thereby affording the desired carbamyloxy compound.

Example 1

Synthesis of N-(3-Methoxycarbonyladamant-1-ylcarbonyl)-L-4-(N,N-dimethylcarbamyloxy) phenylalanine Dimethyl 1,3-adamantanedicarboxylate was monosaponified using 1M NaOH in 3:1 methanol: water. The title compound was prepared using the procedures described in Methods B, L and K.

NMR data was as follows:

$^1$H NMR ($CDCl_3$): δ=9.25 (bs, 1H), 7.12 (d, 2H), 7.03 (d, 2H), 6.37 (d, 1H), 4.86 (m, 1H), 3.65 (s, 3H), 3.22 (m, 2H), 3.09 (s, 3H), 3.00 (s, 3H), 2.10–1.60 (m, 14H).

$^{13}$C NMR($CDC_3$): δ=177.38, 177.21, 173.49, 155.25, 150.37, 133.18, 130.38, 121.62, 52.71, 51.64, 40.89, 40.7, 39.69, 37.85, 37.81, 37.67, 36.55, 36.29, 35.06, 27.65.

Using similar procedures or procedures well-known in the art, Examples 2–26 shown in Table I were prepared.

Example 27

Synthesis of N-(3-Carboxyadamant-1-ylcarbonyl)-(L)-4-(2'-cyanophenyl)phenylalanine Step A: Preparation of 4-Iodo-(L)-phenylalanine Methyl Ester Hydrochloride The title intermediate was prepared from commercially available 4-iodo-)-phenylalanine using Method A.

Step B: Preparation of N-tert-Butyloxycarbonyl-4-iodo-(L)-phenylalanine Methyl Ester The title intermediate was prepared by using the procedure of Schwabacher in *J. Org. Chem*, 59, 15, 1994, 4206.

Step C: Preparation of N-tert-Butylcarbonyl-(L)-4-(trimethylstannyl)phenylalanine Methyl Ester The title intermediate was prepared from N-tert-butyloxycarbonyl-(L)4-iodophenylalanine methyl ester using the procedure described by Morera and Ortar *Synlett* 1997, 1403.

Step D: Preparation of N-tert-Butyloxycarbonyl-(L)4-(2'-cyanophenyl)phenylalanine Methyl Ester To a solution of N-tert-butyloxycarbonyl-(L)-4-(trimethylstannyl)phenylalanine methyl ester in toluene was added 2-bromobenzonitrile (1.0 eq). The solution was degassed under a nitrogen atmosphere. Dichlorobis (triphenylphosphine)palladium (II) (0.03%) was added and the reaction mixture was heated to 100° C. for 2 hours. Additional 2-bromobenzonitrile (1.0 eq) was added and the reaction heated for an additional hour. The reaction was cooled and ethyl acetate was added. The solution was then washed with water and saturated salt solution, dried over magnesium sulfate. The solvent was removed by rotoevaporation and the residue was purified by silica gel chromatography (ethyl acetate/hexanes 1:3), to provide the title compound.

Step E: Preparation of (L)-4-(2'-cyanophenyl)phenylalanine Methyl Ester Trifluoroacetate Salt The title compound was prepared from N-tert-butyloxycarbonyl-(L)4-(2'-cyanophenyl)-phenylalanine methyl ester using Method H.

Step F: Preparation of N-(3-Methoxycarbonyladamant-1-ylcarbonyl)-(L)-4-(2'-cyanophenyl)phenylalanine Methyl Ester The title compound was obtained by coupling of (L)-4-(2'-cyanophenyl)phenylalanine methyl ester trifluoroacetate salt and 3-(methoxycarbonyl)adamantane-1-carboxylic acid using Method J.

Step G: Preparation of N-(3-Methoxycarbonyladamant-1-ylcarbonyl)-(L)-4-(2'-cyanophenyl)phenylalanine The title compound was obtained by hydrolysis of N-(3-methoxycarbonyladamant-1-ylcarbonyl)-(L)-4-(2'-cyanophenyl)phenylalanine methyl ester using Method E.

NMR data were as follows:

$^1$H NMR (CDCl$_3$): δ1.67 (m, 14H); 3.08 (m, 2H); 4.75 (m, 1H); 3.62 (s, 3H); 6.39 (bs, 1H); 7.35 (d, 2H); 7.46 (d, 2H); 7.54 (m, 1H); 7.70 (m, 1H); 7.81 (m, 1H)

Step H: Preparation of N-(3-Carboxyadamant-1-ylcarbonyl)-(L)-4-(2'-cyanophenyl)phenylalanine The title compound was obtained by hydrolysis of N-(3-methoxycarbonyladamant-1-ylcarbonyl)-(L)-4-(2'-cyanophenyl)phenylalanine using Method E.

NMR data were as follows:

$^{13}$C NMR (CDCl$_3$): δ20.72; 27.61; 29.59; 34.99; 36.77; 37.44; 37.66; 39.46; 40.72; 52.97.

Example 28

Synthesis of N-(3-Methoxycarbonyladamant-1-ylcarbonyl)-(L)-4-(2'-methoxyphenyl)phenylalanine Methyl Ester The title compound was prepared in a manner analogous to the procedures described in Example 27 by using the appropriate aryl bromide or iodide in Step D.

NMR data were as follows:

$^1$H NMR (CDCl$_3$): δ7.39 (d, 2H), 7.24 (m, 2H), 7.05 (d, 2H), 6.96 (m, 2H), 6.05 (d, 1H), 4.85 (m, 1H), 3.71 (s, 3H), 3.67 (s, 3H), 3.54 (s, 3H), 3.16–2.99 (m, 2H), 2.07–1.57 (m, 14H).

$^{13}$C NMR (CDCl$_3$): δ177.15, 176.36, 172.25, 156.37, 137.25, 134.36, 130.67, 130.01, 129.56, 128.89, 128.58, 120.74, 111.12, 55.26, 52.50, 52.14, 51.49, 40.83, 40.62, 39.77, 37.90, 37.86, 37.64, 37.16, 35.06, 27.64.

Example 29

Synthesis of N-(3-Methoxycarbonyladamant-1-ylcarbonyl)-(L)-4-(2'-fluorophenyl)phenylalanine Methyl Ester The title compound was prepared in a manner analogous to the procedures described in Example 27 by using the appropriate aryl bromide or iodide in Step D.

NMR data were as follows:

$^1$H NMR (CDCl$_3$): δ7.49–7.08 (m, 8H), 6.11 (d,1H), 4.92 (m,1H), 3.75 (s, 3H), 3.63 (s, 3H), 3.26–3.09 (m, 2H), 2.15–1.65 (m, 14H).

$^{13}$C NMR (CDCl$_3$): δ177.27, 176.45, 172.27, 161.44, 135.40, 134.61, 130.66, 129.46, 129.11, 128.96, 128.46, 124.35, 116.24, 115.94, 52.58, 52.28, 51.60, 40.94, 40.73, 39.87, 38.01, 37.98, 37.73, 37.32, 35.15, 27.72.

Example 30

Synthesis of N-(3-Methoxycarbonyladamant-1-ylcarbonyl)-(L)-4-(1',3'-dimethyl-2',4'-dioxopyrimidin-5-yl)phenylalanine The title compound was prepared in a manner analogous to the procedures described in Example 27 by using the appropriate aryl bromide or iodide in Step D.

NMR data were as follows:

$^1$H NMR (CDCl$_3$): δ7.45 (d, 2H), 7.11 (d, 2H), 6.12 (d, 1H), 4.88 (d, 1H), 3.74 (s, 3H), 3.65 (s, 3H), 3.48 (s, 3H), 3.41 (s, 3H), 3.42 (m, 1H), 3.22 (m, 2H), 2.16–1.66 (m, 14H).

$^{13}$C NMR (CDCl$_3$): δ52.58, 52.23, 51.58, 40.91, 40.70, 39.90, 37.96, 37.73, 37.25, 36.91, 35.13, 28.06, 27.72.

Example 31

Synthesis of N-(3-Methoxycarbonyladamant-1-ylcarbonyl)-(L)-4-(2',4'-dimethoxy-pyrimidin-5-yl)phenylalanine The title compound was prepared in a manner analogous to the procedures described in Example 27 by using the appropriate aryl bromide or iodide in Step D.

NMR data were as follows:

$^1$H NMR (CDCl$_3$): δ8.24 (s, 1H), 7.44 (d, 2H), 7.15 (d, 2H), 6.13 (d, 1H), 4.91 (m, 1H), 4.03 (s, 3H), 4.01 (s, 3H), 3.77 (s, 3H), 3.64 (s, 3H), 3.27 (m, 2H), 2.15–1.66 (m, 14H).

$^{13}$C NMR (CDCl$_3$): δ176.96, 176.16, 171.99, 167.91, 164.31, 157.36, 135.29, 131.90, 129.30, 128.69, 115.56, 54.69, 53.93, 52.53, 52.25, 51.58, 40.91, 40.71, 39.86, 38.00, 37.71, 37.27, 35.13, 27.73.

Example 32

Synthesis of N-(3-Methoxycarbonyladamant-1-ylcarbonyl)-(L)-4-(2'-pyridyl)phenylalanine The title compound was prepared in a manner analogous to the procedures described in Example 27 by using the appropriate aryl bromide or iodide in Step D.

NMR data were as follows:

$^1$H NMR (CDCl$_3$): δ8.61 (d, 1H), 7.88 (d, 2H), 7.67 (m, 1H), 7.17 (d+m, 3H), 6.14 (d, 1H), 4.86 (m, 1H), 3.67 (s, 3H), 3.56 (s, 3H), 3.20 (m, 2H), 2.08–1.58 (m, 14H).

$^{13}$C NMR (CDCl$_3$): δ176.93, 176.20, 171.84, 156.72, 144.43, 137.99, 136.68, 136.62, 129.55, 126.80, 121.47, 120.23, 52.62, 52.19, 51.52, 40.86, 40.67, 39.84, 37.95, 37.91, 37.67, 37.20, 35.09, 27.69.

Example 33

Synthesis of N-(3-Methoxycarbonyladamant-1-ylcarbonyl)-(L)-4-(1'-oxo-2'-pyridyl)phenylalanine Methyl Ester N-(3-Methoxycarbonyladamant-1-ylcarbonyl)-(L)-4-(2'-pyridyl)phenylalanine methyl ester(292 mg, 0.613 mmol) was dissolved in dry dichloromethane with MCPBA (2.0 eq, 395 mg) added over a period of 3 minutes. The reaction mixture was stirred at room temperature overnight, under nitrogen. The organic layer was washed with NaHCO$_3$ saturated solution, and brine, dried over magnesium sulfate. After filtration, the solvent was evaporated under reduced pressure and the crude material was purified on column chromatography with MeOH/CH$_2$Cl$_2$ 5:95, to yield the title compound.

NMR data were as follows:

$^1$H NMR (CDCl$_3$): δ8.28 (m, 1H), 7.75 (d, 2H), 7.41 (m, 1H), 7.30 (m, 1H), 7.21 (m, 1H), 7.17 (d, 2H), 6.19 (d, 1H), 4.87 (m, 1H), 3.70 (s, 3H), 3.59 (s, 3H), 3.21 (m, 2H), 2.10–1.61 (m, 14H).

$^{13}$C NMR (CDCl$_3$): δ176.97, 176.29, 171.83, 148.63, 140.33, 137.62, 131.44, 129.25, 129.07, 127.18, 125.72, 124.39, 52.56, 52.27, 51.55, 40.88, 40.69, 39.83, 37.97, 37.92, 37.69, 37.30, 35.11, 27.70.

Example 34

Synthesis of N-(3-Methoxycarbonyladamant-1-ylcarbonyl)-(L)-4-(1'-oxo-2'-pyridyl)phenylalanine The title compound was prepared using the procedures described herein.

NMR data were as follows:

$^1$H NMR (CDCl$_3$): δ8.41 (d, 1H), 7.50 (d, 2H), 7.66 (m, 1H), 7.54 (m, 2H), 4.75 (m, 1H), 3.62 (s, 3H), 3.36–3.08 (m, 2H), 2.15–1.68 (m, 14H).

Example 35

Synthesis of N-(3-Methoxycarbonyladamant-1-ylcarbonyl)-(L)4-(1'-methyl-2'-oxo-3'-pyridyl) phenylalanine Step A: Preparation of N-(3-Methoxycarbonyladmant-1-ylcarbonyl)-(L)-4-iodophenylalanine Methyl Ester The title compound was obtained by coupling of 3-(methoxycarbonyl)adamantane-1-carboxylic acid and (L)4-iodophenylalanine methyl ester hyrochloride salt using Method J.

Step B: Preparation of 3-Bromo-1-methyl-1H-pyridin-2-one

The title compound was prepared in two steps from 1H-pyridin-2-one using method outline by Tee and Oswald in *J. Am. Chem. Soc.,* 104, 15, 1982, 4142.

Step C: Preparation of N-(3-Methoxycarbonyladamant-1-ylcarbonyl)-(L)-4-(1'-methyl-2'-oxo-3'-pyridyl) phenylalanine Methyl Ester A flask was charged with N-(3-methoxycarbonyladamant-1-ylcarbonyl)-(L)-4-iodophenylalanine methyl ester (144 mg, 0.2 mmol), bis(pinacolato)diboron (1.1 eq, 67 mg), potassium acetate (3.0 eq, 71 mg), and [1,1'-bis (diphenylphosphino)ferrocene]dichloropalladium (II) complex with dichloromethane (1:1) (0.03 eq), and flushed under nitrogen. Upon addition of DMF (10 mL), the reaction mixture was stirred at 80° C. for two hours. After cooling the reaction mixture to room temperature, 3-bromo-1-methyl-1H-pyridin-2-one (2.eq, 90 mg), 2M Na$_2$CO$_3$ (5.0 eq, 600 μL), and [1,1'-bis(diphenylphosphino)ferrocene] dichloropalladium (II) complex with dichloromethane (0.01 eq) were added. The reaction mixture was stirred overnight at 80° C. under nitrogen. The solution was cooled down to room temperature and the product extracted with ether. The organic layer was washed with brine and dried over MgSO$_4$. The crude material was purified on column chromatography (silica gel; EtOAc/hexanes 1:7) to afford the title compound.

NMR data were as follows:

$^1$H NMR (CDCl$_3$): δ7.68 (d, 2H), 7.53 (dd, 1H), 7.36 (dd, 1H), 7.14 (d, 2H), 6.30 (t, 1H), 6.17 (d, 1H), 4.92 (dd, 1H), 3.76 (s, 3H), 3.66 (s, 3H), 3.63 (s, 3H), 3.19 (m, 2H), 2.18–1.68 (m, 14H).

$^{13}$C NMR (CDCl$_3$): δ177.13, 176.36, 172.03, 161.85, 137.54, 135.57, 135.27, 130.84, 129.01, 128.64, 105.89, 52.77, 52.31, 51.67, 41.02, 40.82, 39.94, 38.21, 38.11, 38.04, 37.83, 37.31, 35.25, 27.85, 27.74.

Step D: Preparation of N-(3-Methoxycarbonyladamant-1-ylcarbonyl)-(L)-4-(1'-methyl-2'-oxo-3'-pyridyl) phenylalanine The title compound was obtained by hydrolysis of N-(3-methoxycarbonyladamant-1-ylcarbonyl)-(L)-4-(1'-methyl-2'-oxo-3'-pyridyl)phenylalanine methyl ester using Method E.

Example 36

Synthesis of N-(3-Methoxycarbonyladamant-1-ylcarbonyl)-(L)4-(1'-methyl-2'-oxopiperidin-3'-yl) phenylalanine Methyl Ester The title compound was obtained by hydrogenation of N-(3-methoxycarbonyladamant-1-ylcarbonyl)-(L)-4-(1'-methyl-1'H-pyridin-2'-one-3'-yl)phenylalanine methyl ester using a Parr hydrogenation apparatus. The reaction was run for 48 hours at 50° C. under 50 psi of hydrogen. The reaction mixture was filtered through a pad of Celite and then evaporated under reduced pressure to afford the title compound.

NMR data were as follows:

$^1$H NMR (CDCl$_3$): δ7.13 (d, 2H), 7.03 (d, 2H), 6.08 (d, 1H), 4.87 (m, 1H), 3.72 (s, 3H), 3.60 (2s, 4H), 3.47–3.25 (m, 2H), 3.12 (m, 2H), 3.01 (s, (3H), 2.40–1.56 (m, 18H).

$^{13}$C NMR (CDCl$_3$): δ177.06, 176.22, 171.98, 170.42, 140.34, 133.94, 129.22, 128.30, 52.63, 52.18, 51.58, 50.13, 47.95, 40.94, 40.71, 39.85, 37.73, 37.09, 35.16, 34.91, 30.36, 30.21, 27.75, 20.48.

Example 37

Synthesis of N-(3-Methoxycarbonyladamant-1-ylcarbonyl)-(L)-4-(N,N-dimethylaminocarbonylmethyl)phenylalanine Step A: Preparation of N-(3-Methoxycarbonyladamant-1-ylcarbonyl)-(L)-4-(prop-2-en-1-yl)phenylalanine Methyl Ester The title compound was obtained from N-(3-methoxycarbonyladamant-1-ylcarbonyl)-(L)-4-iodophenylalanine methyl ester using the procedure by Tilley described in *J. Org. Chem.* 1990, 55, 3, 906.

Step B: Preparation of N-(3-Methoxycarbonyladamant-1-ylcarbonyl)-(L)-4-(carboxymethyl)phenylalanine Methyl Ester The title compound was obtained from N-(3-methoxycarbonyladamant-1-ylcarbonyl)-(L)4-(2-propenyl) phenylalanine methyl ester using the procedure by Tilley described in *J. Org. Chem.* 1990, 55, 3, 906.

Step C: Preparation of N-(3-Methoxycarbonyladamant-1-ylcarbonyl)-(L)-4-(N,N-dimethylaminocarbonylmethyl) phenylalanine Methyl Ester The title compound was obtained by coupling of N-(3-methoxycarbonyladamant-1-ylcarbonyl)-(L)-4-(carboxymethyl)phenylalanine methyl ester and dimethylamine hydrochloride salt using Method J.

NMR data were as follows:

$^1$H NMR (CDCl$_3$): δ7.20 (d, 2H), 7.05 (d, 2H), 6.12 (d, 1H), 4.86 (d, 1H), 3.73 (s, 3H), 3.70 (s, 2H), 3.66 (s, 3H), 3.18 (m, 2H), 2.99 (s, 3H), 2.97 (s, 3H), 2.10–1.60 (m, 14H).

$^{13}$C NMR (CDCl$_3$): δ177.19, 176.35, 172.17, 170.99, 134.28, 133.83, 129.53, 128.85, 52.58, 52.15, 51.56, 40.82, 40.61, 40.35, 39.77, 37.92, 37.86, 37.63, 37.10, 35.40, 35.06, 27.63.

Step D: Preparation of N-(3-Methoxycarbonyladamant-1-ylcarbonyl)-(L)-4-(N,N-dimethylaminocarbonylmethyl) phenylalanine The title compound was obtained by hydrolysis of N-(3-methoxycarbonyladamant-1-ylcarbonyl)-(L)-4-(N,N-dimethylaminocarbonylmethyl)phenylalanine methyl ester using Method E.

Example 38

Synthesis of N-(3-Methoxycarbonyladamant-1-ylcarbonyl)-(L)-4-[1,1-difluoro-1-(N,N-dimethylaminocarbonyl)methyl]phenylalanine Step A: Preparation of tert-Butyl 2-(4-Methylphenyl)-2-oxoacetate The title material was prepared using the procedure described in Nimitz in *J. Org. Chem.*, 46, 1, 1981, 211.

Step B: Preparation of tert-Butyl 2,2-Difluoro-2-(4-methylphenyl)acetate

The title material was isolated using the procedure described by Tilley in *J. Med. Chem*, 34, 3, 1991, 1125.

Step C: Preparation of tert-Butyl 2,2-Difluoro-2-(4-bromomethylphenyl)acetate

The title material was isolated using the procedure described by Tilley in *J. Med. Chem*, 34, 3, 1991, 1125.

Step D: Preparation of (3R,5R,6S)-4-(Benzyloxycarbonyl)-5,6-diphenyl-3-[4-(1-tert-butoxycarbonyl-1,1-difluoromethyl)phenylmethyl]-2,3,5,6-tetrahydro4H-oxazin-2-one The title material was isolated using the procedure outlined by Williams in *J. Am. Chem. Soc.*, 113, 24, 1991, 9276.

Step E: Preparation of (3R,5R,6S)-4-(Benzyloxycarbonyl)-5,6-diphenyl-3-[4-(1-N,N-dimethylaminocarbonyl-1,1-difluoromethyl)phenylmethyl]-2,3,5,6-tetrahydro-4H-oxazin-2-one The title material was prepared by Cbz protection followed by Method J.

Step F: Preparation of (L)-4-[1,1-Difluoro-1-(N,N-dimethylaminocarbonyl)-methyl]phenylalanine The title material was isolated using the procedure outline by Williams in *J. Am. Chem. Soc.*, 113, 24, 1991, 9276.

Step G: Preparation of N-(3-Methoxycarbonyladamant-1-ylcarbonyl)-(L)-4-[1,1-difluoro-1-(N,N-dimethylaminocarbonyl)methyl]phenylalanine Methyl Ester The title material was obtained from Step F using Method A and Method J.

NMR data were as follows:

$^1$H NMR (CDCl$_3$): δ7.50 (d, 2H), 7.20 (d, 2H), 6.11 (d, 1H), 4.90 (m, 1H), 3.75 (s, 3H), 3.67 (s, 3H), 3.28 (m, 2H), 3.04 (s, 3H), 2.96 (s, 3H), 2.17–1.67 (m, 14H).

$^{13}$C NMR (CDCl$_3$): δ177.27, 176.54, 172.06, 163.52, 139.16, 132.50, 129.79, 125.50, 115.60, 52.54, 52.43, 51.72, 40.95, 40.77, 39.92, 38.06, 37.74, 37.49, 37.26, 37.19, 37.13, 36.95, 35.14, 27.72.

Step H: Preparation of N-(3-Methoxycarbonyladamant-1-ylcarbonyl)-(L)-4-[1,1-difluoro-1-(N,N-dimethylaminocarbonyl)methyl]phenylalanine The title material was obtained from appropriate starting materials using Method E.

Example 39

Synthesis of Methyl 2-(3-Methoxycarbonyladamant-1-ylcarbonylamino)-3-(4-tert-butoxycarbonylpiperazin-1-yl)propionate Step A: Preparation of Methyl 2-Carbobenzyloxyamino-3-(4-tert-butoxycarbonylpiperazin-1-yl)propionate To N-carbobenzyloxydehydroalanine methyl ester (2.0 g, 8.4 mmol) was added 4-tert-butoxycarbonylpiperazine (1.56 g, 1.0 eq), ferric chloride (0.220 g, 0.2 eq) in a 6:1 mixture of acetonitrile/methanol. The reaction mixture was stirred at room temperature for 2 days. The reaction mixture was evaporated under reduced pressure. EtOAc was added and the organic layer washed with a soldium sulfate solution. Upon removal of the solvent under reduced pressure, the crude material was purified by column chromatography (silica gel; CH$_2$Cl$_2$:MeOH 4:1) to afford the title compound.

Step B: Preparation of Methyl 2-Amino-3-(4-tert-butoxycarbonylpiperazin-1-yl)propionate The title material from Step A was dissolved in methanol with catalytic amount of 10% Pd on C. The reaction mixture was hydrogenated for 2 hours at room temperature in methanol under 25 psi of hydrogen. After filtration of the crude reaction mixture through a pad of Celite, the solvent was evaporated under reduced pressure to afford the title compound.

Step C: Preparation of Methyl 2-(3-Methoxycarbonyladamant-1-ylcarbonylamino)-3-(4-tert-butoxycarbonylpiperazin-1-yl)propionate The tile material was obtained from coupling of 3-(methoxycarbonyl)adamantane-1-carboxylic acid and the title material describe in Step B, using Method I.

NMR data were as follows:

$^1$H NMR (CDCl$_3$): δ6.47 (d, 1H), 4.44 (m, 1H), 3.63 (s, 3H), 3.54 (s, 3H), 3.30 (m, 4H), 2.62 (d, 2H), 2.37 (m, 4H), 2.10–1.58 (m, 14H), 1.33 (s, 9H).

$^{13}$C NMR (CDCl$_3$): δ177.09, 176.70, 172.08, 154.55, 79.48, 57.88, 52.65, 52.08, 51.45, 50.03, 43.00, 40.78, 40.51, 39.80, 37.88, 37.62, 35.03, 28.05, 27.58.

Example 40

Synthesis of Methyl 2-(3-Methoxycarbonyladamant-1-ylcarbonylamino)-3-(piperidin-1-yl)propionate The title compound was prepared according to the procedures described in Example 13 and using piperidine in Step A.

NMR data were as follows:

$^1$H NMR (CDCl$_3$): δ6.78 (d, 1H), 4.37 (m, 1H), 3.64 (s, 3H), 3.57 (s, 3H), 2.63 (m, 2H), 2.40–1.30 (m, 2H).

$^{13}$C NMR (CDCl$_3$): δ177.21, 176.91, 172.31, 58.06, 54.15, 52.02, 51.45, 50.00, 40.83, 40.49, 39.82, 37.85, 37.68, 35.10, 27.66, 25.78, 23.70.

Example 41

Synthesis of Methyl 2-(3-Methoxycarbonyladamant-1-ylcarbonylamino)-3-(piperazin-1-yl)propionate Methyl Ester The title compound described in Example 39 was taken up in neat TFA and the reaction mixture was stirred at room temperature for 1 hour. Upon evaporation of the solvent under reduced pressure, the title compound was isolated as a foam.

NMR data were as follows:

$^1$H NMR (CDCl$_3$): δ4.90 (m, 1H), 3.78 (s, 3H), 3.69 (s, 3H), 3.65–3.45 (m, 10H), 2.20–1.77 (m, 14H).

$^{13}$C NMR (CDCl$_3$): δ178.97, 177.33, 169.77, 159.34, 158.81, 117.22, 113.43, 56.82, 53.18, 51.79, 50.75, 48.94, 41.25, 40.85, 40.69, 39.31, 37.45, 37.34, 37.31, 34.75, 27.85, 26.15.

Example 42

Synthesis of 2-(3-Methoxycarbonyladamant-1-ylcarbonylamino)-3-[4-(N,N-dimethylaminocarbonylmethyl)piperazin-1-yl] propionic Acid Step A: Preparation of Methyl 2-(3-Methoxycarbonyladamant-1-ylcarbonylamino)-3-[4-(N,N-dimethylaminocarbonylmethyl)piperazin-1-yl] propionate Methyl 2-(3-Methoxycarbonyladamant-1-ylcarbonylamino)-3-(piperazin-1-yl)propionate (114 mg, 0.28 mol) was dissolved in anhydrous dichloromethane (10 mL) and Et$_3$N (3.0 eq) and N,N-dimethyl 2-chloroacetamide (3.0 eq) were added. The reaction mixture was refuxed at 50° C. for 4 hours. The solvent was then evaporated under reduced pressure and the crude material was purified by column chromatography (silica gel; CHCl$_3$/MeOH 9:1) to afford the title compound.

Step B: Preparation of 2-(3-Methoxycarbonyladamant-1-ylcarbonylamino)-3-[4-(N,N-dimethylaminocarbonylmethyl)piperazin-1-yl]propionic Acid The title compound was prepared by hydrolysis of the methyl ester from Step A using Method D.

Example 43

Synthesis of (2S)-2-(3-Methoxycarbonyladamant-1-ylcarbonylamino)-3-[4-(N,N-dimethylaminocarbonyloxy)cyclohex-1-yl]propionic Acid Step A: Preparation of tert-Butyl (2S)-2-Amino-3-(4-hydroxycyclohex-1-yl)propionate L-Tyrosine tert-butyl ester (0.6 g) was hydrogenated in MeOH, with 10% Rh/Al$_2$O$_3$ under 50 psi of hydrogen at room temperature for 2 days. The reaction mixture was filtered through Celite and the solvent evaporated under reduced pressure to afford the title intermediate as a foam.

Step B: Preparation of tert-Butyl (2S)-2-(3-Methoxycarbonyladamant-1-ylcarbonylamino)-3-(4-hydroxycyclohex-1-yl)propionate The title compound was obtained by coupling tert-butyl (2S)-2-amino-3-(4-hydroxycyclohex-1-yl)propionate and 3-methoxycarbonyladamantane-1-carboxylic acid using Method I.

Step C: Preparation of tert-Butyl (2S)-2-(3-Methoxycarbonyladamant-1-ylcarbonylamino)-3-[4-(N,N-dimethylaminocarbonyloxy)cyclohex-1-yl)propionate The compound from Step B (1.6 g) was dissolved in anhydrous pyridine (10 mL) and N,N-dimethylcarbamyl chloride (1.2 eq, 0.5 mL) and the reaction was heated at 90° C. for a few hours. Upon cooling, the solvent was evaporated under reduced pressure and EtOAc was added. The organic layer was then washed with brine, dried over MgSO$_4$, filtered and evaporated under reduced pressure. The crude product was purified by column chromatography (silica gel; EtOAc/hexanes 3:7) to afford the title compound.

Step D: Preparation of (2S)-2-(3-Methoxycarbonyladamant-1-ylcarbonylamino)-3-[4-(N,N-dimethylaminocarbonyloxy)cyclohex-1-yl)propionic Acid The product from Step C was dissolved in formic acid at room temperature and the reaction mixture was stirred overnight. After evaporation of the solvent under reduced pressure, the title compound was isolated as a solid.

NMR data were as follows:
$^1$H NMR (CDCl$_3$): δ7.73 (br, 1H), 6.19 (m, 1H), 4.93 (bs, 0.5H), 4.64 (m, 1H), 4.56 (m, 0.5H), 3.71 (s, 3H), 2.95 (s, 3H), 2.92 (s, 3H), 2.30–1.00 (m, 25H).

Example 44

Synthesis of 2S-2-(1-Methoxycarbonyladamant-1-ylcarbonylamino)-3-[4(N,N-dimethylaminocarbonylmethinyl)cyclohex-1-yl] propionic Acid Step A: Preparation of tert-Butyl 2S-2-(3-Methoxycarbonyladamant-1-ylcarbonylamino)-3-(4-oxocyclohex-1-yl)propionate tert-Butyl (2S)-2-(3-Methoxycarbonyladamant-1-ylcarbonylamino)-3-(4-hydroxycyclohex-1-yl)propionate from Example 21, Step B was dissolved in dry dichloromethane and PDC (1.0 eq) was added at room temperature. The reaction mixture was stirred for 5 hours. After evaporation of the solvent under reduced pressure, the crude product was purified by column chromatography (silica gel; EtOAc/hexanes, 1:4) to afford the title compound.

Step B: Preparation of tert-Butyl 2S-2-(3-Methoxycarbonyladamant-1-ylcarbonylamino)-3-[4-(N,N-dimethylaminocarbonylmethinyl)cyclohex-1-yl] propionate Sodium hydride (60% in oil) (1.0 eq, 0.013 g) was dissolved in 0.7 mL of dry THF at room temperature. Dimethyl carbamoylmethylphosphonic acid diethyl ester (1.0 eq, 0.123 g) was added dropwise. The solution became clear. After 10 min. of stirring, the compound from Step A (0.1 g, 0.22 mmol) was added to the reaction mixture. The solution was stirred for another 15 min. The reaction was then quenched with 2 drops of 1M H$_3$PO$_4$. The reaction was concentrated, and the crude residue was purified on a prep plate (silica gel; EtOAc) to afford the title compound.

Step C: Preparation of tert-Butyl 2S-2-(3-Methoxycarbonyladamant-1-ylcarbonylamino)-3-[4-(N,N-dimethylaminocarbonylmethinyl)cyclohex-1-yl] propionate The title compound was prepared by cleavage of the t-butyl ester from Step B, using the method described in Example 21, Step D.

NMR data were as follows:
$^1$H NMR (CDCl$_3$): δ8.15 (s, 1H), 6.38 (d, 1H), 5.75 (s, 1H), 4.67 (m, 1H), 3.71 (s, 3H), 3.08 (s, 3H), 3.06 (s, 3H), 2.75 (m, 1H), 2.40–1.00 (m, 24H).
$^{13}$C NMR (CDCl$_3$): δ177.33, 177.27, 175.19, 169.96, 163.41, 152.13, 151.80, 114.80, 51.80, 50.01, 49.92, 41.12, 40.91, 39.92, 39.73, 38.14, 37.86, 35.73, 35.26, 35.06, 34.26, 33.68, 33.42, 32.75, 29.80, 29.64, 27.88.

Example 45

Synthesis of N-(3-Methoxycarbonyladamant-1-ylcarbonyl)-(L)-Ne-(tert-butoxycarbonyl)lysine Methyl Ester The title compound was prepared by coupling the appropriate starting materials using Method I.

NMR data were as follows:
$^1$H NMR (CDCl$_3$): δ6.31 (d, 1H), 4.97 (br, 1H), 4.59 (m, 1H), 3.74 (s, 3H), 3.67 (s, 3H), 3.09 (bq, 2H), 2.25–1.10 (m, 29H).
$^{13}$C NMR (CDCl$_3$): δ176.94, 176.60, 172.95, 155.88, 78.59, 52.13, 51.52, 51.43, 40.89, 40.66, 39.99, 39.79, 37.98, 37.71, 35.12, 31.86, 29.19, 28.20, 27.72, 22.35.

Example 46

Synthesis of N-(1-Methoxycarbonyladamant-3-ylcarbonyl)-(L)-Nε-(N,N-dimethylaminocarbonyl) lysine Methyl Ester

Step A: Preparation of N-(3-Methoxycarbonyladamant-1-ylcarbonyl)-(L)-lysine Methyl Ester Trifluoroacetate Salt The compound from Example 45, Step A, was hydrolyzed using the procedure described in Example 41 to afford the title intermediate.

Step B: Preparation of N-(3-Methoxycarbonyladamant-1-ylcarbonyl)-(L)-Nε-(N,N-dimethylaminocarbonyl)lysine Methyl Ester The compound from Step A (1 mmol) was dissolved in 10 mL of dry benzene and $Et_3N$ (1.1 eq, 0.7 mL) and N,N-dimethylcarbamyl chloride (1.1 eq, 112 μL) were added. The reaction mixture was refluxed for 4 hours. EtOAc was added and the organic layer washed with saturated $NaHCO_3$, and brine. The organic layer was dried over $MgSO_4$. After filtration and evaporation under reduced pressure, the crude residue was purified by column chromatography (silica gel; EtOAc) to afford the title compound.

Example 47

Synthesis of N-(3-Methoxycarbonyladamant-1-ylcarbonyl)-(L)-Nε-(N,N-dimethylaminocarbonyl) lysine

The title compound was prepared by hydrolysis of the compound of Example 46 using Method E.

NMR data were as follows:
$^1H$ NMR ($CDCl_3$): δ10.80 (br, 1H), 6.64 (d, 1H), 5.30 (br, 1H), 4.56 (q, 1H), 3.63 (s, 3H), 3.15 (m, 2H), 2.88 (s, 6H), 2.20–1.15 (m, 20H).

$^3C$ NMR ($CDCl_3$): δ177.03, 176.86, 173.82, 158.84, 51.52, 40.85, 40.64, 40.23, 37.90, 37.65, 36.08, 35.06, 31.67, 29.50, 27.67, 21.99.

Example 48

Synthesis of N-(3-Methoxycarbonyladamant-1-ylcarbonyl)-(L)-Nδ-(N,N-dimethylaminocarbonyl) ornithine

The title compound was prepared from the appropriate starting materials using the procedures described in Examples 45, 46 and 47.

NMR data were as follows:
$^1H$ NMR ($CDCl_3$): δ10.40 (br, 1H), 6.57 (d, 1H), 5.26 (bs, 1H), 4.53 (q, 1H), 3.60 (s, 3H), 3.22 (m, 2H), 2.86 (s, 6H), 2.18–1.40 (m, 18H).

Example 49

Synthesis of 2-(3-Methoxycarbonyladamant-1-ylcarbonylamino)pent-4-ynoic Acid

Step A: Preparation of tert-Butyl 2-(3-Methoxycarbonyladamant-1-ylcarbonylamino)pent-4-ynoate The title compound was prepared by coupling of appropriate starting materials using Method I.

Step B: Preparation of 2-(3-Methoxycarbonyladamant-1-ylcarbonylamino)pent-4-ynoic Acid The title compound was prepared by hydrolysis of the compound from Step A using formic acid as described in Example 43, Step D.

NMR data were as follows:
$^1H$ NMR ($CDCl_3$): δ8.09 (s, 1H), 6.72 (a, 1H), 4.75 (m, 1H), 3.68 (s, 3H), 2.84 (m, 2H), 2.21 (bs, 2H), 2.09 (m, 1H), 2.02 (s, 2H), 1.87 (bs, 8H), 1.70 (bs, 2H).

$^{13}C$ NMR ($CDCl_3$): δ177.85, 177.56, 173.458, 164.38, 78.14, 71.86, 51.97, 50.36, 41.07, 40.98, 39.63, 37.87, 37.85, 37.74, 35.12, 27.76, 21.89.

Example 50

Synthesis of 2-(3-Methoxycarbonyladamant-1-ylcarbonylamino)-5-(N,N-dimethylaminocarbonyl) pent-4-ynoic Acid

Step A: Preparation of tert-Butyl 2-(3-Methoxycarbonyladamant-1-ylcarbonylamino)-5-(N,N-dimethylaminocarbonyl)pent-4-ynoate The compound from Step A of Example 49 (0.389 g, 1 mmol) was dissolved in dry DMF (5 mL) with dichlorobis(diphenylphosphine)palladium (II) (0.02 eq), CuI (0.02eq), $Et_3N$ (0.4 eq, 3 mL), and N,N-dimethylcarbamyl chloride (1.0 eq, 92 μL). The reaction mixture was stirred overnight at room temperature and then at 70° C. for 1 hour. The mixture was filtered through a pad of Celite and the solvent removed under reduced pressure. The crude product was purified by column chromatography (silica gel; EtOAc/hexanes, 2:3) to afford the title compound.

Step B: Preparation of 2-(3-Methoxycarbonyladamant-1-ylcarbonylamino)-5-(N,N-dimethylaminocarbonyl)pent-4-ynoic Acid The title compound was prepared by hydrolysis of the compound from Step A as described in Example 43, Step D.

NMR data were as follows:
$^1H$ NMR ($CDCl_3$): δ8.14 (s, 1H), 7.29 (d, 1H), 4.82 (m, 1H), 3.71 (s, 3H), 3.26 (s, 3H), 3.10 (d, 2H), 3.05 (s, 3H), 2.30–1.70 (m, 14H).

$^{13}C$ NMR ($CDCl_3$): δ177.83, 177.35, 171.73, 164.03, 155.10, 90.36, 74.88, 51.81, 50.28, 41.07, 40.98, 39.81, 38.66, 37.94, 37.81, 35.22, 34.53, 27.84, 22.17.

Example 51

Synthesis of 2-(3-Methoxycarbonyladamant-1-ylcarbonylamino)-6-(N,N-dimethylaminocarbonyl) hex-4-ynoic Acid

Step A: Preparation of N,N-Dimethyl acetoacetamide

The title intermediate was prepared using the procedure described in Bartlett in *J. Org. Chem,* 47, 7, 1982, 1284.

Step B: Preparation of tert-Butyl 2-(3-Methoxycarbonyladamant-1-ylcarbonylamino)-6-(N,N-dimethylaminocarbonyl)hex-4-ynoate tert-Butyl 2-(3-methoxycarbonyladamant-1-ylcarbonylamino)pent-4-ynoate (0.44 g) was dissolved in 0.8 mL of dry benzene under nitrogen. To this solution was added a catalytic amount of $CuSO_4$ and the reaction mixture was brought to reflux. N,N-Dimethyl acetoacetamide was added dropwise in excess. Evolution of nitrogen was observed. The addition was complete after 30 min. The reaction was then heated for another 30 min. After cooling the reaction mixture, the solvent was evaporated under reduced pressure and the crude product was purified on a prep plate (silica gel; EtOAc/hexanes, 2:3) to afford the title compound as an oil.

Step C: Preparation of 2-(3-Methoxycarbonyladamant-1-ylcarbonylamino)-6-(N,N-dimethylaminocarbonyl)hex4-ynoic Acid The title compound was prepared by hydrolysis of the compound from Step B as described in Example 43, Step D.

NMR data were as follows:

1H NMR (CDCl$_3$): δ6.94 (bd, 1H), 4.73 (bs, 1H), 3.72 (s, 3H), 3.47 (bs, 2H), 3.13 (s, 3H), 3.03 (s, 3H), 2.87 (m, 2H), 2.24 (bs, 2H), 2.13 (bs, 2H), 1.93 (bs, 8H), 1.75 (bs, 2H).

Example 52

Synthesis of 2-(3-Methoxycarbonyladamant-1-ylcarbonylamino)-3-[3-(2'-methoxyphenyl)isoxazol-5-yl]propionic Acid Step A: Preparation of 2-Methoxybenzaldehyde Oxime The title intermediate was prepared as described in Goldschmidt Chem. Ber, 23, 1890, 2740.

Step B: Preparation of tert-Butyl 2-(3-Methoxycarbonyladamant-1-ylcarbonylamino)-3-[3-(2-methoxyphenyl)isoxazol-5-yl]propionate To a solution of 5.25% aqueous NaOCl (1.33 g, 0.77 mmol) in CHCl$_3$ at 0° C. was added a solution of 2-methoxybenzaldehyde oxime (0.77 mmol, 0.116 g) dropwise and tert-butyl 2-(3-methoxycarbonyladamant-1-ylcarbonylamino)pent4-ynoate (300 mg, 0.77 mmol) and one drop of Et$_3$N. After addition, the reaction mixture was allowed to warm up to room temperature and stirred overnight. The solvent was evaporated under reduced pressure and the crude product was purified on a prep plate (silica gel; EtOAc/hexanes, 2:3) to afford the title compound.

Step C: Preparation of 2-(3-Methoxycarbonyladamant-1-ylcarbonylamino)-3-[3-(2'-methoxyphenyl)isoxazol-5-yl]propionic Acid The title compound was prepared by hydrolysis of the compound from Step B as described in Example 43, Step D.

NMR data were as follows:
$^1$H NMR (CDCl$_3$): δ8.11 (s, 1H), 7.81 (t, 1H), 7.43 (t, 1H), 7.02 (m, 2H), 6.73 (d, 1H), 6.64 (s, 1H), 4.95 (bd, 1H), 3.89 (s, 3H), 3.64 (s, 3H), 3.62 (m, 1H), 3.44 (m, 1H), 2.30–1.50 (m, 14H).
$^{13}$C NMR (CDCl$_3$): δ177.89, 177.45, 173.37, 167.42, 164.45, 160.04, 157.19, 131.50, 129.38, 120.93, 117.23, 111.49, 104.96, 55.46, 51.88, 50.88, 41.04, 40.90, 39.63, 37.90, 37.83, 37.73, 35.11, 28.53, 27.77.

Example 53

Synthesis of 2-(3-Methoxycarbonyladamant-1-ylcarbonylamino)-3-[3-(2'-nitrophenyl)isoxazol-5-yl]propionic Acid The title compound was prepared using the procedure described in Example 51 and the appropriate starting materials.

NMR data were as follows:
$^1$H NMR (CDCl$_3$): δ9.83 (br, 1H), 7.91 (d, 1H), 7.67 (m, 3H), 6.69 (, 1H), 6.25 (s, 1H), 4.95 (m, 1H), 3.65 (s, 3H), 3.59 (dd, 1H), 3.42 (dd, 1H), 2.30–1.50 (m, 14H).
$^{13}$C NMR (CDCl$_3$): δ177.89, 177.50, 172.95, 168.77, 159.88, 148.51, 133.03, 131.53, 130.68, 124.46, 123.98, 103.59, 51.88, 50.71, 41.05, 40.95, 39.57, 37.74, 35.10, 28.60, 27.78.

Example 54

Synthesis of 2-(3-Methoxycarbonyladamant-1-ylcarbonylamino)-3-[3-(2'-cyanophenyl)isoxazol-5-yl]propionic Acid The title compound was prepared using the procedure described in Example 51 and the appropriate starting materials.

NMR data were as follows:
$^1$H NMR (CDCl$_3$): δ8.85 (br, 1H), 7.96 (d, 1H), 7.81 (d, 1H), 7.72 (dt, 1H), 6.80 (s, 1H), 6.61 (d, 1H), 5.01 (q, 1H), 3.67 (s, 3H), 3.63 (dd, 1H), 3.49 (dd, 1H), 2.30–1.60 (m, 14H).

Example 55

Synthesis of Methyl 2-(3-Methoxycarbonyladamant-1-ylcarbonylamino)-6-(tert-butoxycarbonylamino)hex-4-ynoate Step A: Preparation of Methyl 2-Amino-6-(tert-butoxycarbonylamino)hex-4-ynoate The title intermediate was prepared from the appropriate starting materials using the procedure described in Nispen in J. R. Neth. Chem. Soc, 102,5,1983,276

Step B: Preparation of Methyl 2-(3-Methoxycarbonyladamant-1-ylcarbonylamino)-6-(tert-butoxycarbonylamino)hex-4-ynoate The title compound was prepared by coupling the appropriate starting materials using Method I.

NMR data were as follows:
$^1$H NMR (CDCl$_3$): δ6.44 (d, 1H), 4.86 (br, 1H), 4.69 (m, (1H), 3.87 (bs, 2H), 3.78 (s, 3H), 3.67 (s, 3H), 2.74 (m, 2H), 2.20 (s, 2H), 2.02 (s, 2H), 1.93 (s, 8H), 1.70 (s, 2H), 1.64 (s, 9H).
$^{13}$C NMR (CDCl$_3$): δ177.19, 176.61, 171.13, 155.25, 79.73, 77.26, 52.69, 51.78, 50.35, 41.06, 40.90, 40.00, 38.07, 38.01, 37.89, 37.84, 35.26, 30.54, 28.28, 27.87, 22.51.

Example 56

Synthesis of Methyl 2-(3-Methoxycarbonyladamant-1-ylcarbonylamino)-6-(N, N-dimethylaminocarbonylamino)hex-4-ynoate The title compound was prepared using the procedure described in Example 46.

NMR data were as follows:
$^1$H NMR (CDCl$_3$): δ6.43 (d, 1H), 4.78 (bt, 1H), 4.64 (m, 1H), 3.89 (m, 2H), 3.70 (s, 3H), 3.59 (s, 3H), 2.85 (s, 6H), 2.20 (m, 2H), 2.20–1.60 (m, 14H).
$^{13}$C NMR (CDCl$_3$): δ177.38, 176.85, 171.36, 157.93, 80.73, 77.09, 52.59, 51.65, 50.38, 40.95, 40.78, 39.90, 37.93, 37.88, 37.76, 37.73, 36.00, 35.13, 30.77, 27.74, 22.54.

Example 57

Synthesis of 2-(3-Methoxycarbonyladamant-1-ylcarbonylamino)-6-(N,N-dimethylaminocarbonylamino)hex4-ynoic Acid The title compound was prepared by hydrolysis of the compound of Example 56 using Method E.

NMR data were as follows:
$^1$H NMR (CDCl$_3$): δ10.0–9.00 (br, 2H), 6.72 (d, 1H), 4.68 (m, 1H), 3.97 (m, 2H), 3.67 (s, 3H), 2.94 (s, 6H), 2.79 (m, 2H), 2.20–1.60 (m, 14H).
$^{13}$C NMR (CDCl$_3$): δ177.33, 177.17, 172.43, 158.42, 79.81, 57.83, 51.76, 50.66, 41.02, 40.86, 39.94, 37.93, 37.87, 37.77, 36.24, 35.18, 31.05, 27.81, 22.51.

Example 58

Synthesis of N-(3-N,N-Dimethylcarbonyladamant-1-ylcarbonyl)-(L)4-(N,N-dimethylcarbamyloxy)phenylalanine Isopropyl Ester The title compound was prepared by coupling the appropriate starting materials using Method I.

NMR data were as follows:

$^1$H NMR (CDCl$_3$): δ7.07 (dd, 4H), 6.11 (d, 1H), 5.02 (m, 1H), 4.73 (m, 1H), 3.09 (s, 5H), 3.02 (s, 6H), 2.98 (s, 3H), 2.15–1.64 (m, 14H), 1.21 (d, 6H).

$^{13}$C NMR (CDCl$_3$): δ176.56, 175.82, 171.16, 150.63, 132.81, 130.17, 121.64, 69.34, 52.73, 41.86, 41.10, 39.62, 38.44, 38.09, 37.77, 37.71, 36.88, 35.30, 28.19, 21.58.

Example 59

Synthesis of N-(3-N,N-Dimethylcarbonyladamant-1-ylcarbonyl)-(L)-4-(N,N-dimethylcarbamyloxy) phenylalanine The title compound was prepared by hydrolysis of the compound of Example 58 in isopropanol/water (1:1) at room temperature overnight. EtOAc was added and the aqueous layer acidified to pH 2.0 with 1N HCl. Additional EtOAc was then added and the organic layer was dried over MgSO$_4$. After filtration and evaporation of the solvent under reduced pressure, the title compound was isolated as a foam.

NMR data were as follows:

$^1$H NMR (CDCl$_3$): δ7.34 (d, 1H), 7.20 (d, 2H), 6.99 (d, 2H), 4.60 (m, 1H), 3.30–3.00 (m, 2H), 3.10 (s, 3H), 3.06 (s, 3H), 2.97(s, 3H), 2.67 (s, 3H), 2.10–168 (m, 15H).

$^{13}$C NMR (CDCl$_3$): δ145.79, 120.11, 125.44, 116.72, 49.04, 37.34, 36.43, 35.97, 35.17, 34.06, 33.09, 32.78, 31.31, 30.76, 30.62, 30.41, 29.26, 23.84, 23.44.

Example 60

Synthesis of N-(3-Acetyladamnant-1-ylcarbonyl)-(L)4-(N,N-dimethylcarbamyloxy)phenylalanine Isopropyl Ester Step A: Preparation of 3-Methoxycarbonyladamantane-1-carboxylic Acid Chloride 3-Methoxycarbonyladamantane-1-carboxylic acid (1.0 eq) was suspended in a solution of CH$_2$Cl$_2$ containing a catalytic amount of DMF. This mixture was then cooled to 0° C. and oxalyl chloride (3.0 eq) was added. After 15 minutes, the reaction mixture was allowed to warm to room temperature and stirred at this temperature for 30 minutes, and then warmed to reflux for 1 hour. During the reflux period, the reaction became homogenous. The reaction mixture was then cooled and concentrated at reduced pressure. The residue was taken-up in diethyl ether and filtered. The filtrate was concentrated at reduced pressure to yield the title intermediate as a yellow liquid.

Step B: Preparation of Methyl 3-Acetyladamantane-1-carboxylate

Under nitrogen, a chilled (0° C.) diethyl ether suspension of copper (1) iodide (3.0 eq) was treated with methyl lithium (6.0 eq, 1.4 M in ethyl ether). The resulting solution was chilled to −78° C. and after ten minutes a chilled (−30° C.) diethyl ether solution of 3-methoxycarbonyladamantane-1-carboxylic acid chloride was added dropwise over a five minute period. The reaction was stirred for 45 minutes at −78° C. and then quenched with MeOH (11.0 eq) and allowed to warm to room temperature. After addition of Et$_2$O and saturated aqueous ammonium chloride solution, the mixture was stirred for ten minutes and then the organic phase was washed with saturated NH$_4$Cl, saturated NaHCO$_3$, brine, dried (MgSO$_4$), filtered and concentrated to a volatile oil, which was used without further purification.

Step C: Preparation of 3-Acetyladamantane-1-carboxylic Acid

The title intermediate was prepared from the compound of Step B using Method E.

Step D: Preparation of N-(3-Acetyladamant-1-ylcarbonyl)-(L)4-(N,N-dimethylcarbamyloxy)phenylalanine Isopropyl Ester The title compound was prepared from the appropriate starting materials using Method I.

NMR data were as follows:

$^1$H NMR (CDCl$_3$): δ7.08 (dd, 4H), 6.10 (d, 1H), 5.07 (m, 1H), 4.76 (m, 1H), 3.02 (m, 5H), 2.98 (s, 3H), 2.17, (m, 2H), 2.09 (s, 3H), 1.84–1.65 (m, 12H), 1.23 (d, 6H).

$^{13}$C NMR (CDCl$_3$): δ213.00, 176.48, 171.22, 150.64, 132.80, 130.20, 121.68, 69.41, 52.70, 46.59, 40.73, 39.36, 38.02, 37.11, 36.90, 36.52, 36.28, 35.23, 37.75, 24.30, 21.60, 21.56.

Example 61

Synthesis of N-(3-Acetyladamant-1-ylcarbonyl)-(L)-4-(N,N-dimethylcarbamyloxy)phenylalanine The title compound was prepared from the compound of Example 60 using Method E.

Example 62

Synthesis of N-[3-(1-Hydroxyeth-1-yl)adamant-1-ylcarbonyl]-(L)-4-(N,N-dimethylcarbamyloxy) phenylalanine Isopropyl Ester The compound of Example 60 (1.0 eq) was dissolved in MeOH and treated with NaBH$_4$ (2.0 eq). The reaction mixture was stirred at room temperature for one hour and then concentrated. The residue was taken-up in 0.1 N HCl and the product extracted with ethyl acetate. The combined organic extracts were washed with brine, dried MgSO$_4$, filtered and concentrated, and the crude product was purified by preparative thin layer chromatography (EtOAc/hexanes) to yield the title compound.

NMR data were as follows:

$^1$H NMR (CDCl$_3$): δ7.10 (m, 4H), 6.06 (m, 1H), 5.07 (m, 1H), 4.78 (m, 1H), 3.28 (m, 1H), 3.05 (m, 5H), 2.99 (s, 3H), 2.12 (m, 2H), 1.74–1.41 (m, 12H), 1.25 (d, 6H), 1.09 (d, 3H).

13C NMR (CDCl$_3$): δ177, 171.47, 158, 151, 132.99, 130.31, 121.76, 75.06, 69.39, 52.52, 41.07, 39.26, 39.18, 38.72, 38.62, 37.10, 36.95, 36.61, 36.33, 35.99, 28.07, 21.67, 16.47.

Example 63

Synthesis of N-[3-(1-Hydroxyeth-1-yl)adamant-1-ylcarbonyl]-(L)-4-(N,N-dimethylcarbamyloxy) phenylalanine The title compound was prepared from the compound of Example 41 using Method E.

Example 64

Synthesis of N-(3-Methoxycarbonyladamant-1-ylcarbonyl)-(L)-4-[2-(N,N-dimethylaminocarbonyl) ethen-1-yl]phenylalanine Methyl Ester Step A: Preparation of N-tert-butoxycarbonyl-(L)-4-(trifluoromethylsulfonyloxy)phenyalanine Methyl Ester N-tert-Butoxycarbonyl-L-tyrosine methyl ester was converted to the title compound using the method described in Tilley et al., *J. Org. Chem.* 1990, 55, 906–910.

Step B: Preparation of N-tert-Butoxycarbonyl-(L)-4-[2-(N,N-dimethylaminocarbonyl)ethen-1-yl]phenylalanine Methyl Ester A solution the compound from Step A (1.0 eq), N,N-dimethylacrylamide (2.0 eq) and triethylamine (6.0 eq) in DMF was degassed with nitrogen and then dichlorobis(triphenylphosphine)-palladium(II) (0.04 eq.) was added. The reaction was warmed to 90° C. under a stream of nitrogen for 16 hours. The reaction mixture was cooled and diluted with EtOAc and water and washed with 0.2 N citric acid, water, saturated NaHCO$_3$, brine, dried (MgSO$_4$), filtered and concentrated. The residue was chromatographed on a silica gel column using ethyl acetate/hexanes to yield the title compound.

Step C: Preparation of (L)-4-[2-(N,N-dimethylaminocarbonyl)ethen-1-yl]phenylalanine Methyl Ester Trifluoroacetic Acid Salt The compound from Step B was dissolved in methylene chloride and treated with trifluoroacetic acid for approximately five hours. The reaction mixture was then concentrated to afford the title compound.

Step D: Preparation of N-(3-Methoxycarbonyladamant-1-ylcarbonyl)-(L)-4-[2-(N,N-dimethylaminocarbonyl)ethen-1-yl]phenylalanine Methyl Ester The title compound was prepared by coupling the appropriate starting materials using Method I.

NMR data were as follows:

$^1$H NMR (CDCl$_3$): δ7.63 (d, 1H), 7.45 (d, 2H), 7.07 (d, 2H), 6.87 (1H), 6.06 (d, 1H), 4.89–4.86 (m, 1H), 3.75 (s, 3H), 3.66 (s, 3H), 3.18–3.01 (m, 8H), 2.16 (m, 2H), 1.91–1.54 (m, 12H).

$^{13}$C NMR (CDCl$_3$): δ177.1, 176.2, 172.0, 166.6, 141.7, 137.5, 134.2, 129.7, 127.9, 117.3, 52.6, 52.4, 51.7, 41.0, 40.8, 40.0, 38.1, 37.8, 37.6, 35.2, 27.8.

Example 65

Synthesis of Methyl 2-(3-Methoxycarbonyladamant-1-ylcarbonylamino)-3-[2-(N,N-dimethylaminocarbonylamino)thiazol-4-yl]propionate Step A: Preparation of Methyl 3-(2-Aminothiazol-4-yl)-2-(tert-butoxycarbonylamino)propionate The title intermediate was prepared using the procedure described in Leanna Tett.Lett, 34,28, 1993,4485.

Step B: Preparation of Methyl 3-[2-(N,N-Dimethylaminocarbonylamino)thiazol-4-yl]-2-(tert-butoxycarbonylamino)propionate The title compound was prepared from the compound of Step A using the procedure described in Example 46, Step B.

Step C: Preparation of Methyl 3-[2-(N,N-Dimethylaminocarbonylamino)thiazol-4-yl]-2-aminopropionate Trifluoroacetic Acid Salt The title compound was prepared from the compound of Step B using the procedure described in Example 64, Step C.

Step D: Preparation of Methyl 2-(3-Methoxycarbonyladamant-1-ylcarbonylamino)-3-[2-(N,N-dimethylaminocarbonylamino)thiazol-4-yl]propionate The title compound was prepared by coupling the appropriate starting materials using Method J.

Example 66

Synthesis of 2-(3-Methoxycarbonyladamant-1-ylcarbonylamino)-3-[2-(N,N-dimethylaminocarbonylamino)thiazol-4-yl]propionic Acid The title compound was prepared by hydrolysis of the compound from Example 65 using Method D.

Example 67

Synthesis of N-(1-Methoxycarbonyladamant-3-ylcarbonyl)-(L)-4-pyridylalanine Methyl Ester The title compound was prepared by coupling the appropriate starting materials using Method I.

NMR data were as follows:

$^1$H NMR (CDCl$_3$): δ8.52 (d, 2H), 7.02 (d, 2H) 6.10 (d, 1H), 4.89 (q, 1H), 3.75 (s, 3H), 3.66 (s, 3H), 3.21 (dd, 1H), 3.07 (dd, 1H), 2.16 (bs, 2H), 60–2.00 (m, 14H).

$^{13}$C NMR (CDCl$_3$): δ52.55, 52.03, 51.75, 40.95, 40.81, 39.89, 38.06, 37.73, 37.09, 35.13, 27.71.

Example A

In vitro Assay For Determining Binding of Candidate Compounds to VLA-4

An in vitro assay was used to assess binding of candidate compounds to $\alpha_4\beta_1$ integrin. Compounds which bind in this assay can be used to assess VCAM-1 levels in biological samples by conventional assays (e.g., competitive assays). This assay is sensitive to IC$_{50}$ values as low as about 1 nM.

The activity of $\alpha_4\beta_1$ integrin was measured by the interaction of soluble VCAM-1 with Jurkat cells (e.g., American Type Culture Collection Nos. TIB 152, TIB 153, and CRL 8163), a human T-cell line which expresses high levels of $\alpha_4\beta_1$ integrin. VCAM-1 interacts with the cell surface in an $\alpha_4\beta_1$ integrin-dependent fashion (Yednock, et al. J. Biol. Chem., 1995, 270:28740).

Recombinant soluble VCAM-1 was expressed as a chimeric fusion protein containing the seven extracellular domains of VCAM-1 on the N-terminus and the human IgG$_1$ heavy chain constant region on the C-terminus. The VCAM-1 fusion protein was made and purified by the manner described by Yednock, supra.

Jurkat cells were grown in RPMI 1640 supplemented with 10% fetal bovine serum, penicillin, streptomycin and glutamine as described by Yednock, supra.

Jurkat cells were incubated with 1.5 mM MnCl$_2$ and 5 μg/mL 15/7 antibody for 30 minutes on ice. Mn$^{+2}$ activates the receptor to enhance ligand binding, and 15/7 is a monoclonal antibody that recognizes an activated/ligand occupied conformation of $\alpha_4\beta_1$ integrin and locks the molecule into this conformation thereby stabilizing the VCAM-1/$\alpha_4\beta_1$ integrin interaction. Yednock, et al., supra. Antibodies similar to the 15/7 antibody have been prepared by other investigators (Luque, et al, 1996, J. Biol. Chem. 271:11067) and may be used in this assay.

Cells were then incubated for 30 minutes at room temperature with candidate compounds, in various concentrations ranging from 66 μM to 0.01 μM using a standard 5-point serial dilution. 15 μL soluble recombinant VCAM-1 fusion protein was then added to Jurkat cells and incubated for 30 minutes on ice. (Yednock et al., supra.).

Cells were then washed two times and resuspended in PE-conjugated goat F(ab')$_2$ anti-mouse IgG Fc (Immunotech, Westbrook, Me.) at 1:200 and incubated on ice, in the dark, for 30 minutes. Cells were washed twice and analyzed with a standard fluorescence activated cell sorter ("FACS") analysis as described in Yednock, et al., supra.

Compounds having an IC$_{50}$ of less than about 15 μM possess binding affinity to $\alpha_4\beta_1$.

When tested in this assay, each of the compound prepared in the above examples has or is expected to have an IC$_{50}$ of 15 μM or less (or is expected to be active in vivo)

Example B

In vitro Saturation Assay For Determining Binding of Candidate Compounds to $\alpha_4\beta_1$ The following describes an in vitro assay to determine the plasma levels needed for a compound to be active in the Experimental Autoimmune Encephalomyelitis ("EAE") model, described in the next example, or in other in vivo models.

Log-growth Jurkat cells are washed and resuspended in normal animal plasma containing 20 µg/ml of the 15/7 antibody (described in the above example).

The Jurkat cells are diluted two-fold into either normal plasma samples containing known candidate compound amounts in various concentrations ranging from 66 µM to 0.01 µM, using a standard 12 point serial dilution for a standard curve, or into plasma samples obtained from the peripheral blood of candidate compound-treated animals.

Cells are then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody.

The cells are then exposed to phycoerythrin-conjugated goat F(ab')$_2$ anti-mouse IgG Fc (Immunotech, Westbrook, Me.), which has been adsorbed for any non-specific cross-reactivity by co-incubation with 5% serum from the animal species being studied, at 1:200 and incubated in the dark at 4° C. for 30 minutes.

Cells are washed twice with assay medium and resuspended in the same. They are then analyzed with a standard fluorescence activated cell sorter ("FACS") analysis as described in Yednock et al. J. Biol. Chem., 1995, 270:28740.

The data is then graphed as fluorescence versus dose, e.g., in a normal dose-response fashion. The dose levels that result in the upper plateau of the curve represent the levels needed to obtain efficacy in an in vivo model.

This assay may also be used to determine the plasma levels needed to saturate the binding sites of other integrins, such as the $\alpha_9\beta_1$ integrin, which is the integrin most closely related $\alpha_4\beta_1$ (Palmer et al, 1993, J. Cell Bio., 123:1289). Such binding is predictive of in vivo utility for inflammatory conditions mediated by $\alpha_9\beta_1$ integrin, including by way of example, airway hyper-responsiveness and occlusion that occurs with chronic asthma, smooth muscle cell proliferation in atherosclerosis, vascular occlusion following angioplasty, fibrosis and glomerular scarring as a result of renal disease, aortic stenosis, hypertrophy of synovial membranes in rheumatoid arthritis, and inflammation and scarring that occur with the progression of ulcerative colitis and Crohn's disease.

Accordingly, the above-described assay may be performed with a human colon carcinoma cell line, SW 480 (ATTC #CCL228) transfected with cDNA encoding $\alpha_9$ integrin (Yokosaki et al., 1994, J. Biol. Chem., 269:26691), in place of the Jurkat cells, to measure the binding of the $\alpha_9\beta_1$ integrin. As a control, SW 480 cells which express other $\alpha$ and $\beta_1$ subunits may be used.

Accordingly, another aspect of this invention is directed to a method for treating a disease in a mammalian patient, which disease is mediated by $\alpha_9\beta_1$, and which method comprises administering to said patient a therapeutically effective amount of a compound of this invention. Such compounds are preferably administered in a pharmaceutical composition described herein above. Effective daily dosing will depend upon the age, weight, condition of the patient which factors can be readily ascertained by the attending clinician. However, in a preferred embodiment, the compounds are administered from about 20 to 500 µg/kg per day.

Example C

In vivo Evaluation

The standard multiple sclerosis model, Experimental Autoimmune (or Allergic) Encephalomyelitis ("EAE"), was used to determine the effect of candidate compounds to reduce motor impairment in rats or guinea pigs. Reduction in motor impairment is based on blocking adhesion between leukocytes and the endothelium and correlates with anti-inflammatory activity in the candidate compound. This model has been previously described by Keszthelyi et al., Neurology, 1996, 47:1053–1059, and measures the delay of onset of disease.

Brains and spinal cords of adult Hartley guinea pigs were homogenized in an equal volume of phosphate-buffered saline. An equal volume of Freund's complete adjuvant (100 mg *mycobacterium tuberculosis* plus 10 ml Freund's incomplete adjuvant) was added to the homogenate. The mixture was emulsified by circulating it repeatedly through a 20 ml syringe with a peristaltic pump for about 20 minutes.

Female Lewis rats (2–3 months old, 170–220 g) or Hartley guinea pigs (20 day old, 180–200 g) were anesthetized with isoflurane and three injections of the emulsion, 0.1 ml each, were made in each flank. Motor impairment onset is seen in approximately 9 days.

Candidate compound treatment began on Day 8, just before onset of symptoms. Compounds were administered subcutaneously ("SC"), orally ("PO") or intraperitoneally ("IP"). Doses were given in a range of 10 mg/kg to 200 mg/kg, bid, for five days, with typical dosing of 10 to 100 mg/kg SC, 10 to 50 mg/kg PO, and 10 to 100 mg/kg IP.

Antibody GG5/3 against $\alpha_4\beta_1$ integrin (Keszthelyi et al., Neurology, 1996, 47:1053–1059), which delays the onset of symptoms, was used as a positive control and was injected subcutaneously at 3 mg/kg on Day 8 and 11.

Body weight and motor impairment were measured daily. Motor impairment was rated with the following clinical score:

| | |
|---|---|
| 0 | no change |
| 1 | tail weakness or paralysis |
| 2 | hindlimb weakness |
| 3 | hindlimb paralysis |
| 4 | moribund or dead |

A candidate compound was considered active if it delayed the onset of symptoms, e.g., produced clinical scores no greater than 2 or slowed body weight loss as compared to the control.

Example D

Asthma Model

Inflammatory conditions mediated by $\alpha_4\beta_1$ integrin include, for example, airway hyper-responsiveness and occlusion that occurs with chronic asthma. The following describes an asthma model which can be used to study the in vivo effects of the compounds of this invention for use in treating asthma.

Following the procedures described by Abraham et al, J. Clin. Invest, 93:776–787 (1994) and Abraham et al, Am J. Respir Crit Care Med, 156:696–703 (1997), both of which are incorporated by reference in their entirety. Compounds of this invention are formulated into an aerosol and administered to sheep which are hypersensitive to *

—O—Z—$R^7$ wherein $R^6$ and $R^{6'}$ are independently selected from the group consisting of hydrogen, alkyl, substituted alkyl, cycloalkyl, substituted cycloalkyl, heterocyclic, substituted heterocyclic, and where $R^6$ and $R^{6'}$ are joined to form a heterocycle or a substituted heterocycle, $R^7$ is selected from the group consisting of heterocycle and substituted heterocycle, and Z is selected from the group consisting of —C(O)— and —SO$_2$—, Ar is aryl, heteroaryl, substituted aryl or substituted heteroaryl, x is an integer of from 1 to 4; and (b) $Ar^1$—$Ar^2$—$C_{1-10}$alkyl-, $Ar^1$—$Ar^2$—$C_{2-10}$alkenyl- and $Ar^1$—$Ar^2$—$C_{2-10}$alkynyl-, wherein $Ar^1$ and $Ar^2$ are independently aryl or heteroaryl each of which is optionally substituted with one to four substituents independently selected from $R^b$; alkyl, alkenyl and alkynyl are optionally substituted with one to four substituents independently selected from $R^a$;

$R^2$ is selected from the group consisting of hydrogen, $C_{1-10}$ alkyl, $C_{2-10}$ alkenyl, $C_{2-10}$ alkynyl, aryl, aryl $C_{1-10}$alkyl, heteroaryl, and heteroaryl $C_{1-10}$ alkyl, wherein alkyl, alkenyl and alkynyl are optionally substituted with one to four substituents selected from $R^a$, and aryl and heteroaryl are optionally substituted with one to four substituents independently selected from $R^b$;

$R^3$ is selected from the group consisting of hydrogen, $C_{1-10}$ alkyl optionally substituted with one to four substituents independently selected from $R^a$ and Cy optionally substituted with one to four substituents independently selected from $R^b$;

$R^a$ is selected from the group consisting of Cy, —$OR^d$, —NO$_2$, halogen, —S(O)$_m R^d$, —$SR^d$, —S(O)$_2 OR^d$, —S(O)$_m NR^d R^e$, —$NR^d R^e$, —O(CR$^f R^g$)$_n NR^d R^e$, —C(O)$R^d$, —CO$_2 R^d$, —CO$_2$(CR$^f R^g$)$_n$CONR$^d R^e$, —OC(O)$R^d$, —CN, —C(O)NR$^d R^e$, —NR$^d$C(O)$R^e$, —OC(O)NR$^d R^e$,—NR$^d$C(O)OR$^e$,—NR$^d$C(O)NR$^d R^e$, —CR$^d$(N—OR$^e$), CF$_3$, and —OCF$_3$; wherein Cy is optionally substituted with one to four substituents independently selected from $R^c$;

$R^b$ is selected from the group consisting of $R^a$, $C_{1-10}$ alkyl, $C_{2-10}$ alkenyl, $C_{2-10}$ alkynyl, aryl $C_{1-10}$ alkyl, heteroaryl, $C_{1-10}$ alkyl, wherein alkyl, alkenyl, aryl, heteroaryl are optionally substituted with a group independently selected from $R^c$;

$R^c$ is selected from the group consisting of halogen, amino, carboxy, $C_{1-4}$ alkyl, $C_{1-4}$ alkoxy, aryl, aryl $C_{1-4}$ alkyl, hydroxy, CF$_3$, and aryloxy;

$R^d$ and $R^e$ are independently selected from hydrogen, $C_{1-10}$ alkyl, $C_{2-10}$ alkenyl, $C_{2-10}$ alkynyl, Cy and Cy—$C_{1-10}$alkyl, wherein alkyl, alkenyl, alkynyl and Cy are optionally substituted with one to four substituents independently selected from $R^c$; or $R^d$ and $R^e$ together with the atoms to which they are attached form a heterocyclic ring of 5 to 7 members containing 0–2 additional heteroatoms independently selected from oxygen, sulfur and nitrogen;

$R^f$ and $R^g$ are independently selected from hydrogen, $C_{1-10}$ alkyl, Cy and Cy—$C_{1-10}$ alkyl; or $R^f$ and $R^g$ together with the carbon to which they are attached form a ring of 5 to 7 members containing 0–2 heteroatoms independently selected from oxygen, sulfur and nitrogen;

Cy is cycloalkyl, heterocyclyl, aryl, or heteroaryl;

m is an integer from 1 to 2;

n is an integer from 1 to 10;

Y is selected from the group consisting of hydrogen, $R^d$, Cy, —$OR^d$, —NO$_2$, halogen, —S(O)$_m R^d$, —$SR^d$, —S(O)$_2 OR^d$, —S(O)$_m NR^d R^e$, —$NR^d R^e$; —O(CR$^f R^g$)$_n NR^d R^e$, —C(O)$R^d$, —CH(OH)$R^d$, —CO$_2 R^d$, —CO$_2$(CR$^f R^g$)$_n$CONR$^d R^e$, —OC(O)$R^d$, —CN, —C(O)NR$^d R^e$, —NR$^d$C(O)$R^e$, —OC(O)NR$^d R^e$, —NR$^d$C(O)OR$^e$, —NR$^d$C(O)NR$^d R^e$, —CR$^d$(N—OR$^e$), CF$_3$, and —OCF$_3$; wherein Cy is optionally substituted with one to four substituents independently selected from $R^c$;

$R^4$ is selected from the group consisting of alkyl, substituted alkyl, alkoxy, substituted alkoxy, acyl, acylamino, thiocarbonyl-amino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where each R is independently hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, —N[S(O)$_2$—R']$_2$ and —N[S(O)$_2$—NR']$_2$ where each R' is independently selected from the group consisting of alkyl, substituted alkyl, aryl, substituted aryl, heteroaryl, substituted heteroaryl, heterocyclic and substituted heterocyclic, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkyl groups having amino groups blocked by conventional blocking groups or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl; or R$^b$;

X$^2$ is selected from the group consisting of hydroxyl, alkoxy, substituted alkoxy, alkenoxy, substituted alkenoxy, cycloalkoxy, substituted cycloalkoxy, cycloalkenoxy, substituted cycloalkenoxy, aryloxy, substituted aryloxy, heteroaryloxy, substituted heteroaryloxy, heterocyclyloxy, substituted heterocyclyloxy and —NR"R" where each R" is independently selected from the group consisting of hydrogen, alkyl, substituted alkyl, alkenyl, substituted alkenyl, cycloalkyl, substituted cycloalkyl, aryl, substituted aryl, heteroaryl, substituted heteroaryl, heterocyclic and substituted heterocyclic; or R$^d$;

v is an integer ranging from 0 to 3; and pharmaceutically acceptable salts thereof.

2. A method for binding VLA-4 in a biological sample which method comprises contacting the biological sample with a compound of claim 1 under conditions wherein said compound binds to VLA-4.

3. A pharmaceutical composition comprising a pharmaceutically acceptable carrier aid a therapeutically effective amount of one or more of a compound of claim 1.

4. A method for the treatment of an inflammatory disease in a patient mediated by VLA-4 which method comprises administering to the patient the pharmaceutical compositions of claim 3.

5. The compound according to claim 1 wherein R$^1$ is selected from (a) —(CH$_2$)$_x$—Ar—R$^5$ where R$^5$ is selected from the group consisting of —O—Z—NR$^6$R$^{6'}$ and —O—Z—R$^7$ wherein R$^6$ and R$^{6'}$ are independently selected from the group consisting of hydrogen, alkyl, substituted alkyl, cycloalkyl, substituted cycloalkyl, heterocyclic, substituted heterocyclic, and where R$^6$ and R$^{6'}$ are joined to form a heterocycle or a substituted heterocycle, R$^7$ is selected from the group consisting of heterocycle and substituted heterocycle, and Z is selected from the group consisting of —C(O)— and —SO$_2$—, Ar is aryl, heteroaryl, substituted aryl or substituted heteroaryl, and x is an integer of from 1 to 4.

6. The compound according to claim wherein R$^1$ is selected from the group consisting of:
3-[(CH$_3$)$_2$NC(O)O-]benzyl,
4-[(CH$_3$)$_2$NC(O)O-]benzyl,
4-[(CH$_3$)$_2$NS(O)$_2$O-]benzyl,
4-[(piperidin-1'-yl)C(O)O-]benzyl,
4-[(piporidin-4'-yl)C(O)O-]benzyl,
4-[(1'-methylpiperidin-4'-yl)C(O)O-]benzyl,
4-[(4'-hydroxypiperidin-1'-yl)C(O)O-]benzyl,
4-[(4'-formyloxypiperidin-1'-yl)C(O)O-]benzyl,
4-[(4'-elboxycarbonylpiperidin-1'-yl)C(O)O-]benzyl,
4-[(4'-carboxylpiperidin-1'-yl)C(O)O-]benzyl,
4-[(3'-hydroxymethylpiperidin-1'-yl)C(O)O-]benzyl,
4-[(4'-hyroxymethylpiperidin-1'-yl)C(O)O-]benzyl,
4-[(4'-phenyl-1'-Boc-piperidin-4'-yl)—C(O)O-]benzyl,
4-[(4'-piperidon-1'-yl ethylene ketal)C(O)O-]benzyl,
4-[(piperazin-4'-y)—C(O)O-]benzy),
4-[(1'-Boc-piperazin-4'-yl)—C(O)O-]benzyl,
4-[(4'-methylpiperazin-1'-yl)C(O)O-]benzyl,
4-[(4'-methylhomopiperazin-1'-yl)C(O)O-]benzyl,
4-[(4'-(2-hydroxyethyl)piperazin-1'-yl)C(O)O-]benzyl,
4-[(4'-phenylpiperazin-1-y])C(O)O-]benzyl,
4-[(4'-(pyridin-2-yl)piperazin-1'-yl)C(O)O-]benzyl,
4-[(4'-(4-trifluoromethylpyridin-2-yl)piperazin-1'-yl)C(O)O-]benzyl,
4-[(4'-(pyrimidin-2-yl)piperazin-1'-yl)C(O)O-]benzyl,
4-[(4'-acetylpiperazin-1'-yl)C(O)O-]benzyl,
4-[(4'-(phenylC(O)-)piperazin-1'-yl)C(O)O-]benzyl,
4-[(4'-(pyridin-4-yl]C(O)-)piperazin-1'-yl)C(O)O-]benzyl,
4-[(4'-(phenylNHC(O)-)piperazin-1'-yl)C(O)O-]benzyl,
4-[(4'-(phenylNHC(S)-)piperazin-1'-yl)C(O)O-]benzyl,
4-[(4'-methanesulfonylpiperazin-1'-yl-C(O)O-)benzyl,
4-[(4'-trifluoromethanesulfonylpiperazin-1'-yl-C(O)O-)benzyl,
4-[(morpholin-4'-yl)C(O)O-]benzyl,
3-nitro-4-[(morpholin-4'-yl)—C(O)O-]benzyl,
4-[(thiomorpholin-4'-yl)C(O)O-]benzyl,
4-[(thiomorpholin-4'-yl sulfone)-C(O)O-]benzyl,
4-[(pyrrolidin-1'-yl)C(O)O-]benzyl,
4-[(2'-methylpyrrolidin-1'-yl)C(O)O-]benzyl,
4-[(2'-(methoxycarbonyl)pyrrolidin-1'-yl)C(O)O-]benzyl,
4-[(2'-(hydroxymethyl)pyrrolidin-1'-yl)C(O)O-]benzyl,
4-[(2'-(N,N-dimethylamino)ethyl)(CH$_3$)NC(O)O-]benzyl,
4-[(2'-(N-methyl-N-toluene-4-sulfonylamino)ethyl)(CH$_3$)N—C(O)O-]benzyl,
4-[(2'-(morpholin-4'-yl)ethyl)(C$_3$)NC(O)O-]benzyl,
4-[(2'-(hydroxy)ethyl)(CH$_3$)NC(O)O-]benzyl,
4-[bis(2'-(hydroxy)ethyl)NC(O)O-]benzyl,
4-[(2'-(formyloxy)ethyl)(CH$_3$)NC(O)O-]benzyl,
4-[(CH$_3$OC(O)CH$_2$)HNC(O)O-]benzyl,
4-[2'-(phenylNHC(O)O-)ethyl-]HNC(O)O-]benzyl,
3-chloro-4-[(CH$_3$)$_2$NC(O)O-]benzyl,
3-chloro-4-[(4'-methylpiperazin-1'-yl)C(O)(O)-]benzyl,
3-chloro-4-[(4'-(pyridin-2-yl)piperazin-1'-yl)C(O)O-]benzyl,
3-chloro-4-((thiomorpholin-4'-yl)C(O)O-benzyl, and
3-fluoro-4-[(CH$_3$)$_2$NC(O)O-]benzyl.

7. The compound according to claim 1, wherein R$^1$ is —CH$_2$—Ar$^2$—Ar$^1$.

8. The compound according to claim 1, wherein R$^2$ is hydrogen.

9. The compound according to claim 1, wherein R$^3$ is hydrogen.

10. The compound according to claim 1, wherein X$^2$ is hydroxyl or alkoxy.

11. The compound according to claim 1, wherein Y is selected from the group consisting of: hydrogen, —C(O)OR$^d$, —S(O)$_m$R$^d$, —C(O)NR$^d$R$^h$, —NR$^d$C(O)OR$^e$, —C(O)R$^d$ and —CH(OH)R$^d$.

12. The compound according to claim 11 wherein Y is —C(O)OR$^d$ and where R$^d$ is hydrogen or alkyl.

13. The compound according to claim 1 wherein the compound of formula II is selected from the group consisting of:

N-(adamant-1-ylcarbonyl)-L-4-(N,N-dimethylcarbamyloxy)phenylalanine tert-butyl ester;
N-(adamant-1-ylcarbonyl)-L-4-(N,N-dimethylcarbamyloxy)phenylalanine;
N-(3-methoxycarbonyladamant-1-ylcarbonyl)-L-4-(N,N-dimethylcarbamyloxy)phenylalanine;
N-(3-methoxycarbonyladamant-1-ylcarbonyl)-L-4-(N,N-dimethylcarbamyloxy)phenylalanine tert-butyl ester;
N-[3-(N-benzyl-N-methylaminocarbonyl)adamant-1-ylcarbonyl]-L-4-(N,N-dimethylcarbamyloxy) phenylalanine tert-butyl ester;
N-(adamant-1-ylcarbonyl)-L-4-(1,1-dioxothiomorpholin-4-ylcarbonyloxy)phenylalanine;

N-[3-(N-benzyl-N-methylaminocarbonyl)adamant-1-ylcarbonyl]-L-4-(N,N-dimethylcarbamyloxy)phenylalanine;
N-(3-methoxycarbonyladamant-1-ylcarbonyl)-L-4-(N,N-dimethylcarbamyloxy)phenylalanine ethyl ester;
N-(3-carboxyadamant-1-ylcarbonyl)-L-4-(N,N-dimethylcarbamyloxy)phenylalanine tert-butyl ester;
N-(3-carboxyadamant-1-ylcarbonyl)-L-4-(N,N-dimethylcarbamyloxy)phenylalanine;
N-(3-tert-butoxycarbonyladamant-1-ylcarbonyl)-L-4-(N,N-dimethylcarbamyloxy)phenylalanine;
N-(3-isopropoxycarbonyladamant-1-ylcarbonyl)-L-4-(N,N-dimethylcarbamyloxy)phenylalanine;
N-[3-(N-methylaminocarbonyl)adamant-1-ylcarbonyl]-L-4-(N,N-dimethylcarbamyloxy)phenylalanine;
N-[3-(aminocarbonyl)adamant-1-ylcarbonyl]-L-4-(N,N-dimethylcarbamyloxy)phenylalanine;
N-(3-methylcarbonyladamant-1-ylcarbonyl)-L-4-(N,N-dimethylcarbamyloxy)phenylalanine;
N-(3-methoxycarbonylaminoadamant-1-ylcarbonyl)-L-4-(N,N-dimethylcarbamyloxy)phenylalanine;
N-(3-methylcarbonyladamant-1-ylcarbonyl)-L-4-(N,N-dimethylcarbamyloxy)phenylalanine methyl ester;
N-[3-(1-hydroxyethyl)adamant-1-ylcarbonyl]-L-4-(N,N-dimethylcarbamyloxy)phenylalanine;
N-(3-methoxycarbonyladamant-1-ylcarbonyl)-L-4-(piperazin-1-ylcarbonyloxy)phenylalanine;
N-(3-methoxycarbonyladamant-1-ylcarbonyl)-L4-(4-methylpiperazin-1-ylcarbonyloxy)phenylalanine;
N-(3-methoxycarbonyladamant-1-ylcarbonyl)-L-4-(4-methylpiperazin-1-ylcarbonyloxy)phenylalanine isopropyl ester;
N-(3-methoxycarbonyladamant-1-ylcarbonyl)-L-4-(piperazin-1-ylcarbonyloxy)phenylalanine isopropyl ester;
N-(3-methoxycarbonyladamant-1-ylcarbonyl)-L-4-(4-methylpiperazin-1-ylcarbonyloxy)phenylalanine tert-butyl ester;
N-(3-methoxycarbonyladamant-1-ylcarbonyl)-L-4-(1-methyl-2-pyridone-3-ylcarbonyloxy)phenylalanine benzyl ester;
N-(3-methoxycarbonyladamant-1-ylcarbonyl)-L-4-(1-methyl-2-pyridone-3-ylcarbonyloxy)phenylalanine;
N-(3-methoxycarbonyladamant-1-ylcarbonyl)-L-4-(N,N-dimethylcarbamyloxy)phenylalanine;
N-(3-carboxyadamant-1-ylcarbonyl)-(L)-4-(2'-cyanophenyl)phenylalanine;
N-(3-methoxycarbonyladamant-1-ylcarbonyl)-(L)-4-(2'-methoxyphenyl)phenylalanine methyl ester;
N-(3-methoxycarbonyladamant-1-ylcarbonyl)-(L)-4-(2'-fluorophenyl)phenylalanine methyl ester;
N-(3-methoxycarbonyladamant-1-ylcarbonyl)-(L)-4-(1',3'-dimethyl-2',4'-dioxopyrimidin-5-yl)phenylalanine;
N-(3-methoxycarbonyladamant-1-ylcarbonyl)-(L)-4-(2',4'-dimethoxy-pyrimidin-5-yl)phenylalanine;
N-(3-methoxycarbonyladamant-1-ylcarbonyl)-(L)-4-(2'-pyridyl)phenylalanine;
N-(3-methoxycarbonyladamant-1-ylcarbonyl)-(L)-4-(1'-oxo-2'-pyridyl)phenylalanine methyl ester;
N-(3-methoxycarbonyladamant-1-ylcarbonyl)-(L)-4-(1'-oxo-2'-pyridyl)phenylalanine;
N-(3-methoxycarbonyladamant-1-ylcarbonyl)-(L)-4-(1'-methyl-2'-oxo-3'-pyridyl)phenylalanine;
N-(3-methoxycarbonyladamant-1-ylcarbonyl)-(L)-4-(1'-methyl-2'-oxopiperidin-3'-yl)phenylalanine methyl ester;
N-(3-methoxycarbonyladamant-1-ylcarbonyl)-(L)-4-(N,N-dimethylaminocarbonylmethyl)phenylalanine;
N-(3-methoxycarbonyladamant-1-ylcarbonyl)-(L)-4-[1,1-difluoro-1-(N,N-dimethylaminocarbonyl)methyl]phenylalanine;
Methyl 2-(3-methoxycarbonyladamant-1-ylcarbonylamino)-3-(4-tert-butoxycarbonylpiperazin-1-yl)propionate;
Methyl 2-(3-methoxycarbonyladamant-1-ylcarbonylamino)-3-(piperidin-1-yl)propionate;
Methyl 2-(3-methoxycarbonyladamant-1-ylcarbonylamino)-3-(piperazin-1-yl)propionate methyl ester;
2-(3-methoxycarbonyladamant-1-ylcarbonylamino)-3-[4-(N,N-dimethylaminocarbonylmethyl)piperazin-1-yl]propionic acid;
(2S)-2-(3-methoxycarbonyladamant-1-ylcarbonylamino)-3-[4-(N,N-dimethylaminocarbonyloxy)cyclohex-1-yl]propionic acid;
2S-2-(1-methoxycarbonyladamant-1-ylcarbonylamino)-3-[4-(N,N-dimethylaminocarbonylmethinyl)cyclohex-1-yl]propionic acid;
N-(3-methoxycarbonyladamant-1-ylcarbonyl)-(L)-Nε-(tert-butoxycarbonyl)lysine methyl ester;
N-(1-methoxycarbonyladamant-3-ylcarbonyl)-(L)-Nε-(N,N-dimethylaminocarbonyl)lysine methyl ester;
N-(3-methoxycarbonyladamant-1-ylcarbonyl)-(L)-Nε-(N,N-dimethylaminocarbonyl)lysine;
N-(3-methoxycarbonyladamant-1-ylcarbonyl)-(L)-Nδ-(N,N-dimethylaminocarbonyl)ornithine;
2-(3-methoxycarbonyladamant-1-ylcarbonylamino)pent-4-ynoic acid;
2-(3-methoxycarbonyladamant-1-ylcarbonylamino)-5-(N,N-dimethylaminocarbonyl)pent-4-ynoic acid;
2-(3-methoxycarbonyladamant-1-ylcarbonylamino)-6-(N,N-dimethylaminocarbonyl)hex-4-ynoic acid;
2-(3-methoxycarbonyladamant-1-ylcarbonylamino)-3-[3-(2'-methoxyphenyl)isoxazol-5-yl]propionic Acid;
2-(3-methoxycarbonyladamant-1-ylcarbonylamino)-3-[3-(2'-nitrophenyl)isoxazol-5-yl]propionic acid;
2-(3-methoxycarbonyladamant-1-ylcarbonylamino)-3-[3-(2'-cyanophenyl)isoxazol-5-yl]propionic acid;
Methyl 2-(3-methoxycarbonyladamant-1-ylcarbonylamino)-6-(tert-butoxycarbonylamino)hex-4-ynoate;
Methyl 2-(3-methoxycarbonyladamant-1-ylcarbonylamino)-6-(N,N-dimethylaminocarbonylamino)hex-4-ynoate;
2-(3-methoxycarbonyladamant-1-ylcarbonylamino)-6-(N,N-dimethylaminocarbonylamino)hex-4-ynoic acid;
N-(3-N,N-dimethylcarbonyladamant-1-ylcarbonyl)-(L)-4-(N,N-dimethylcarbamyloxy)phenylalanine isopropyl ester;
N-(3-N,N-dimethylcarbonyladamant-1-ylcarbonyl)-(L)-4-(N,N-dimethylcarbamyloxy)phenylalanine;
N-(3-acetyladamant-1-ylcarbonyl)-(L)-4-(N,N-dimethylcarbamyloxy)phenylalanine isopropyl ester;
N-(3-acetyladamant-1-ylcarbonyl)-(L)-4-(N,N-dimethylcarbamyloxy)phenylalanine;
N-[3-(1-hydroxyeth-1-yl)adamant-1-ylcarbonyl]-(L)-4-(N,N-dimetdimethylcarbamyloxy)phenylalanine isopropyl ester;
N-[3-(1-hydroxyeth-1-yl)adamant-1-ylcarbonyl]-(L)-4-(N,N-dimethylcarbamyloxy)phenylalanine;
N-(3-methoxycarbonyladamant-1-ylcarbonyl)-(L)-4-[2-(N,N-dimethylaminocarbonyl)ethen-1-yl]phenylalanine methyl ester;
Methyl 2-(3-methoxycarbonyladamant-1-ylcarbonylamino)-3-[2-(N,N-dimethylaminocarbonylamino)thiazol-4-yl]propionate;

2-(3-methoxycarbonyladamant-1-ylcarbonylamino)-3-[2-(N,N-dimethylaminocarbonylamino)thiazol-4-yl]propionic acid; and N-(1-methoxycarbonyladamant-3-ylcarbonyl)-(L)-4-pyridylalanine methyl ester.

14. The pharmaceutical composition according to claim 3 comprising a pharmaceutically acceptable carrier and a therapeutically acceptable effective amount of one or more of a compound selected from the group consisting of:

N-(adamant-1-ylcarbonyl)-L-4-(N,N-dimethylcarbamyloxy)phenylalanine tert-butyl ester;

N-(adamant-1-ylcarbonyl)-L-4-(N,N-dimethylcarbamyloxy)phenylalanine;

N-(3-methoxycarbonyladamant-1-ylcarbonyl)-L-4-(N,N-dimethylcarbamyloxy)phenylalanine;

N-(3-methoxycarbonyladamant-1-ylcarbonyl)-L-4-(N,N-dimethylcarbamyloxy)phenylalanine tert-butyl ester;

N-[3-(N-benzyl-N-methylaminocarbonyl)adamant-1-ylcarbonyl]-L-4-(N,N-dimethylcarbamyloxy)phenylalanine tert-butyl ester;

N-(adamant-1-ylcarbonyl)-L-4-(1,1-dioxothiomorpholin-4-ylcarbonyloxy)phenylalanine;

N-[3-(N-benzyl-N-methylaminocarbonyl)adamant-1-ylcarbonyl]-L-4-(N,N-dimethylcarbamyloxy)phenylalanine;

N-(3-methoxycarbonyladamant-1-ylcarbonyl)-L-4-(N,N-dimethylcarbamyloxy)phenylalanine ethyl ester;

N-(3-carboxyadamant-1-ylcarbonyl)-L-4-(N,N-dimethylcarbamyloxy)phenylalanine tert-butyl ester;

N-(3-carboxyadamant-1-ylcarbonyl)-L-4-(N,N-dimethylcarbamyloxy)phenylalanine;

N-(3-tert-butoxycarbonyladamant-1-ylcarbonyl)-L-4-(N,N-dimethylcarbamyloxy)phenylalanine;

N-(3-isopropoxycarbonyladamant-1-ylcarbonyl)-L-4-(N,N-dimethylcarbamyloxy)phenylalanine;

N-[3-(N-methylaminocarbonyl)adamant-1-ylcarbonyl]-L-4-(N,N-dimethylcarbamyloxy)phenylalanine;

N-[3-(aminocarbonyl)adamant-1-ylcarbonyl]-L-4-(N,N-dimethylcarbamyloxy)phenylalanine;

N-(3-methylcarbonyladamant-1-ylcarbonyl)-L-4-(N,N-dimethylcarbamyloxy)phenylalanine;

N-(3-methoxycarbonylaminoadamant-1-ylcarbonyl)-L-4-(N,N-dimethylcarbamyloxy)phenylalanine;

N-(3-methylcarbonyladamant-1-ylcarbonyl)-L-4-(N,N-dimethylcarbamyloxy)phenylalanine methyl ester;

N-[3-(1-hydroxyethyl)adamant-1-ylcarbonyl]-L-4-(N,N-dimethylcarbamyloxy)phenylalanine;

N-(3-methoxycarbonyladamant-1-ylcarbonyl)-L-4-(piperazin-1-ylcarbonyloxy)phenylalanine;

N-(3-methoxycarbonyladamant-1-ylcarbonyl)-L4-(4-methylpiperazin-1-ylcarbonyloxy)phenylalanine;

N-(3-methoxycarbonyladamant-1-ylcarbonyl)-L-4-(4-methylpiperazin-1-ylcarbonyloxy)phenylalanine isopropyl ester;

N-(3-methoxycarbonyladamant-1-ylcarbonyl)-L-4-(piperazin-1-ylcarbonyloxy)phenylalanine isopropyl ester;

N-(3-methoxycarbonyladamant-1-ylcarbonyl)-L-4-(4-methylpiperazin-1-ylcarbonyloxy)phenylalanine tert-butyl ester;

N-(3-methoxycarbonyladamant-1-ylcarbonyl)-L-4-(1-methyl-2-pyridone-3-yl)phenylalanine benzyl ester;

N-(3-methoxycarbonyladamant-1-ylcarbonyl)-L-4-(1-methyl-2-pyridone-3-yl)phenylalanine;

N-(3-Methoxycarbonyladamant-1-ylcarbonyl)-L-4-(N,N-dimethylcarbamyloxy)phenylalanine;

N-(3-carboxyadamant-1-ylcarbonyl)-(L)-4-(2'-cyanophenyl)phenylalanine;

N-(3-methoxycarbonyladamant-1-ylcarbonyl)-(L)-4-(2'-methoxyphenyl)phenylalanine methyl ester;

N-(3-methoxycarbonyladamant-1-ylcarbonyl)-(L)4-(2'-fluorophenyl)phenylalanine methyl ester;

N-(3-methoxycarbonyladamant-1-ylcarbonyl)-(L)-4-(1',3'-dimethyl-2',4'-dioxopyrimidin-5-yl)phenylalanine;

N-(3-methoxycarbonyladamant-1-ylcarbonyl)-(L)-4-(2',4'-dimethoxy-pyrimidin-5-yl)phenylalanine;

N-(3-methoxycarbonyladamant-1-ylcarbonyl)-(L)-4-(2'-pyridyl)phenylalanine;

N-(3-methoxycarbonyladamant-1-ylcarbonyl)-(L)-4-(1'-oxo-2'-pyridyl)phenylalanine methyl ester;

N-(3-methoxycarbonyladamant-1-ylcarbonyl)-(L)-4-(1'-oxo-2'-pyridyl)phenylalanine;

N-(3-methoxycarbonyladamant-1-ylcarbonyl)-(L)-4-(1'-methyl-2'-oxo-3'-pyridyl)phenylalanine;

N-(3-methoxycarbonyladamant-1-ylcarbonyl)-(L)-4-(1'-methyl-2'-oxopiperidin-3'-yl)phenylalanine Methyl Ester;

N-(3-methoxycarbonyladamant-1-ylcarbonyl)-(L)-4-(N,N-dimethylaminocarbonylmethyl)phenylalanine;

N-(3-methoxycarbonyladamant-1-ylcarbonyl)-(L)-4-[1,1-difluoro-1-(N,N-dimethylaminocarbonyl)methyl]phenylalanine;

Methyl 2-(3-methoxycarbonyladamant-1-ylcarbonylamino)-3-(4-tert-butoxycarbonylpiperazin-1-yl)propionate;

Methyl 2-(3-methoxycarbonyladamant-1-ylcarbonylamino)-3-(piperidin-1-yl)propionate;

Methyl 2-(3-methoxycarbonyladamant-1-ylcarbonylamino)-3-(piperazin-1-yl)propionate methyl ester;

2-(3-methoxycarbonyladamant-1-ylcarbonylamino)-3-[4-(N,N-dimethylaminocarbonylmethyl)piperazin-1-yl]propionic acid;

(2S)-2-(3-methoxycarbonyladamant-1-ylcarbonylamino)-3-[4-(N,N-dimethylaminocarbonyloxy)cyclohex-1-yl]propionic acid;

2S-2-(1-methoxycarbonyladamant-1-ylcarbonylamino)-3-[4-(N,N-dimethylaminocarbonylmethinyl)cyclohex-1-yl]propionic acid;

N-(3-methoxycarbonyladamant-1-ylcarbonyl)-(L)-Nε-(tert-butoxycarbonyl)lysine methyl ester;

N-(1-methoxycarbonyladamant-3-ylcarbonyl)-(L)-Nε-(N,N-dimethylaminocarbonyl)lysine methyl ester;

N-(3-methoxycarbonyladamant-1-ylcarbonyl)-(L)-Nε-(N,N-dimethylaminocarbonyl)lysine;

N-(3-methoxycarbonyladamant-1-ylcarbonyl)-(L)-Nδ-(N,N-dimethylaminocarbonyl)ornithine;

2-(3-methoxycarbonyladamant-1-ylcarbonylamino)pent-4-ynoic acid;

2-(3-methoxycarbonyladamant-1-ylcarbonylamino)-5-(N,N-dimethylaminocarbonyl)pent-4-ynoic acid;

2-(3-methoxycarbonyladamant-1-ylcarbonylamino)-6-(N,N-dimethylaminocarbonyl)hex-4-ynoic acid;

2-(3-methoxycarbonyladamant-1-ylcarbonylamino)-3-[3-(2'-methoxyphenyl)isoxazol-5-yl]propionic acid;

2-(3-methoxycarbonyladamant-1-ylcarbonylamino)-3-[3-(2'-nitrophenyl)isoxazol-5-yl]propionic acid;

2-(3-methoxycarbonyladamant-1-ylcarbonylamino)-3-[3-(2'-cyanophenyl)isoxazol-5-yl]propionic acid;

Methyl 2-(3-methoxycarbonyladamant-1-ylcarbonylamino)-6-(tert-butoxycarbonylamino)hex-4-ynoate;

Methyl 2-(3-methoxycarbonyladamant-1-ylcarbonylamino)-6-(N,N-dimethylaminocarbonylamino)hex-4-ynoate;

2-(3-methoxycarbonyladamant-1-ylcarbonylamino)-6-(N,N-dimethylaminocarbonylamino)hex-4-ynoic acid;

N-(3-N,N-dimethylcarbonyladamant-1-ylcarbonyl)-(L)-4-(N,N-dimethylcarbamyloxy)phenylalanine isopropyl ester;

N-(3-N,N-dimethylcarbonyladamant-1-ylcarbonyl)-(L)-4-(N,N-dimethylcarbamyloxy)phenylalanine;

N-(3-acetyladamant-1-ylcarbonyl)-(L)-4-(N,N-dimethylcarbamyloxy)phenylalanine isopropyl ester;

N-(3-acetyladamant-1-ylcarbonyl)-(L)-4-(N,N-dimethylcarbamyloxy)phenylalanine;

N-[3-(1-hydroxyeth-1-yl)adamant-1-ylcarbonyl]-(L)-4-(N,N-dimethylcarbamyloxy)phenylalanine isopropyl ester;

N-[3-(1-hydroxyeth-1-yl)adamant-1-ylcarbonyl]-(L)-4-(N,N-dimethylcarbamyloxy)phenylalanine;

N-(3-methoxycarbonyladamant-1-ylcarbonyl)-(L)-4-[2-(N,N-dimethylaminocarbonyl)ethen-1-yl]phenylalanine methyl ester;

Methyl 2-(3-methoxycarbonyladamant-1-ylcarbonylamino)-3-[2-(N,N-dimethylaminocarbonylamino)thiazol-4-yl]propionate;

N-(quinuclidin-2-ylcarbonyl)-L-4-(N,N-dimethylcarbamyloxy)phenylalanine; and pharmaceutically acceptable salts thereof.

\* \* \* \* \*

UNITED STATES PATENT AND TRADEMARK OFFICE
CERTIFICATE OF CORRECTION

PATENT NO.         : 6,465,513 B1
APPLICATION NO. : 09/489157
DATED              : October 15, 2002
INVENTOR(S)        : Francine S. Grant et al.

It is certified that error appears in the above-identified patent and that said Letters Patent is hereby corrected as shown below:

IN THE CLAIMS:

Claim 14 at column 78, lines 7-8, delete "N-(quinuclidin-2-ylcarbonyl)-L-4-(N,N-dimethycarbamyloxy)phenylalanine;".

Signed and Sealed this

Twenty-seventh Day of November, 2007

JON W. DUDAS
*Director of the United States Patent and Trademark Office*